(12) United States Patent
Zou et al.

(10) Patent No.: US 11,376,289 B2
(45) Date of Patent: Jul. 5, 2022

(54) COMPOSITION AND USES THEREOF

(71) Applicant: BGI SHENZHEN, Guangdong (CN)

(72) Inventors: Yuanqiang Zou, Shenzhen (CN); Liang Xiao, Shenzhen (CN); Xiaoping Li, Shenzhen (CN); Jinghong Yu, Shenzhen (CN); Chuan Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 0 days.

(21) Appl. No.: 17/059,884

(22) PCT Filed: May 31, 2018

(86) PCT No.: PCT/CN2018/089319
§ 371 (c)(1),
(2) Date: Nov. 30, 2020

(87) PCT Pub. No.: WO2019/227418
PCT Pub. Date: Dec. 5, 2019

(65) Prior Publication Data
US 2021/0220415 A1    Jul. 22, 2021

(51) Int. Cl.
*A61K 35/74*        (2015.01)
*A61K 35/747*       (2015.01)
*A23L 33/135*       (2016.01)
*A61P 1/00*         (2006.01)

(52) U.S. Cl.
CPC .......... *A61K 35/747* (2013.01); *A23L 33/135* (2016.08); *A61P 1/00* (2018.01)

(58) Field of Classification Search
None
See application file for complete search history.

(56) References Cited

U.S. PATENT DOCUMENTS

| 9,028,841  | B2  | 5/2015  | Henn et al. |
| 9,610,307  | B2* | 4/2017  | Berry ................... A61K 35/747 |
| 11,160,837 | B2* | 11/2021 | Zou ........................ A61P 1/00 |
| 2017/0151291 | A1 | 6/2017 | Henn et al. |

FOREIGN PATENT DOCUMENTS

| CN | 104159588   | A  | 11/2014 |
| CN | 104735999   | A  | 6/2015  |
| CN | 104740138   | A  | 7/2015  |
| CN | 107075588   | A  | 8/2017  |
| CN | 107708704   | A  | 2/2018  |
| CN | 107996979   | A  | 5/2018  |
| WO | 2016086206  | A1 | 6/2016  |
| WO | 2017031985  | A1 | 3/2017  |
| WO | 2017205981  | A1 | 12/2017 |

OTHER PUBLICATIONS

Felton et al (Expert Opinion on Drug Delivery. 2013 10 (4): 421-35).*
https://en.wikipedia.org/wiki/Film_coating#:~:text=The%20thickness%20of%20such%20a,applied%20in%20orally%2Dadministered%20pharmaceuticals. Feb. 2014.*
International Search Report issued for PCT/CN2018089319, dated Feb. 27, 2019.
Written Opinion of the International Searching Authority issued for PCT/CN2018089319, dated Feb. 27, 2019.
Office Action issued for JP application No. 2020-566957, dated Feb. 1, 2022, with English translation.
Search Report issued for EP application No. 18920574.3, dated Jan. 17, 2022.
Geirnaert, A. et al. "Butyrate-producing bacteria supplemented in vitro to Crohn's disease patient microbiota increased butyrate production and enhanced intestinal epithelial barrier integrity" Scientific Reports (2017) 7: 11450.
Van Immerseel, F. et al. "Butyric acid-producing anaerobic bacteria as a novel probiotic treatment approach for inflammatory bowel disease" Journal of Medical Microbiology (2010) 59(Pt 2) 141-143.

* cited by examiner

*Primary Examiner* — Jennifer E Graser
(74) *Attorney, Agent, or Firm* — Westman, Champlin & Koehler, P.A.; Z. Peter Sawicki; Manda M. Prose

(57) ABSTRACT

Provided are a composition and the uses thereof. Said composition comprises *Megamonas funimormis* and/or a metabolite thereof, as well as *Anaerofustis stercorihominis* and/or a metabolite thereof. Said composition can efficiently treat and prevent inflammation, specifically ulcerative colitis, and related diseases thereof by using a combination of *Megamonas funimormis* and *Anaerofustis stercorihominis*, and is safe, efficient, exhibits low toxicity and does not easily produce resistance.

20 Claims, 1 Drawing Sheet

Specification includes a Sequence Listing.

SEQUENCE LISTING

<160> NUMBER OF SEQ ID NOS: 7

<210> SEQ ID NO 1
<211> LENGTH: 20

```
<212> TYPE: DNA
<213> ORGANISM: Artificial Sequence
<220> FEATURE:
<223> OTHER INFORMATION: synthetic primer

<400> SEQUENCE: 1
agagtttgat catggctcag                                                     20

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
tagggttacc ttgttacgac tt                                                  22

<210> SEQ ID NO 3
<211> LENGTH: 1423
<212> TYPE: DNA
<213> ORGANISM: Artificial Sequence
<220> FEATURE:
<223> OTHER INFORMATION: Megamonas funiformis AF24-28AC 16S rDNA

<400> SEQUENCE: 3
ttaacacatg caagtcgaac ggggtgttta tttcggtaaa caccaagtgg cgaacgggtg          60
agtaacgcgt aagcaatcta ccttcaagat ggggacaaca cttcgaaagg ggtgctaata        120
ccgaatgaat gtaagagtat cgcatgagac acttactaaa ggaggcctct gaaaatgctt        180
ccgcttgaag atgagcttgc gtctgattag ctagttggtg agggtaaagg cccaccaagg        240
cgacgatcag tagccggtct gagaggatga acggccacat tgggactgag acacggccca        300
gactcctacg ggaggcagca gtggggaatc ttccgcaatg ggcgaaagcc tgacggagca        360
acgccgcgtg aacgatgaag gtcttaggat cgtaaagttc tgttgttagg acgaagggt         420 aagaataata atacggtttt tatttgacgg tacctaacga ggaagccacg gctaactacg        480
tgccagcagc cgcggtaata cgtaggcggc aagcgttgtc cggaattatt gggcgtaaag        540
ggagcgcagg cggaaaacta agcggatctt aaaagtgcgg ggctcaaccc cgtgatgggg        600
tccgaactgg ttttcttgag tgcaggagag gaaagcggaa ttcccagtgt agcggtgaaa        660
tgcgtagata ttgggaagaa caccagtggc gaaggcggct ttctggactg taactgacgc        720
tgaggctcga aagctagggt agcgaacggg attagatacc ccggtagtcc tagccgtaaa        780
cgatggatac taggtgtggg aggtatcgac cccttccgtg ccgagttaa cgcaataagt         840 atcccgcctg gggagtacgg ccgcaaggtt gaaactcaaa ggaattgacg ggggcccgca        900
caagcggtgg agtatgtggt ttaattcgac gcaacgcgaa gaaccttacc aagacttgac        960
attgattgaa aggcctagag ataggtccct tctcttcgga gaacaagaaa acaggtggtg       1020
catggctgtc gtcagctcgt gtcgtgagat gttgggttaa gtcccgcaac gagcgcaacc       1080
cctatactat gttgccagca ttacggatgg gaactcatag tagactgccg cggacaacgc       1140
ggaggaaggc ggggatgacg tcaagtcatc atgcccctta cgtcttgggc tacacacgta       1200
ctacaatggg atgaacagag ggaagcgaaa tcgcgaggtg gagcggatcc ctaaaagcat       1260
ctctcagttc ggattgtagg ctgaaactcg cctacatgaa gtcggaatcg ctagtaatcg       1320
caggtcagca tactgcggtg aatacgttcc cgggccttgt acacaccgcc cgtcacacca       1380
cgaaagtcat tcacacccga agccggctaa gggcctatgg tac                         1423
```

<210> SEQ ID NO 4
<211> LENGTH: 1425
<212> TYPE: DNA
<213> ORGANISM: Artificial Sequence
<220> FEATURE:
<223> OTHER INFORMATION: Anaerofustis stercorihominis AM25-6 16S rDNA

<400> SEQUENCE: 4

| | | | | |
|---|---|---|---|---|
| acgaacgctg | gcggcgtgct | taacacatgc | aagtcgaacg | agaagcttat aaatgatcct | 60 |
| tcgggtgaag | ctataagcgg | acagtggcga | acgggtgagt | aacgcgtagg taaccaacct | 120 |
| catgcagggg | gatagcccag | ggaaacttgg | attaaaccog | cataagacca cagcaccgca | 180 |
| tggtgcaggg | gtaaaaactc | cggtggcatg | agacggacct | gcgtcttatt aggtagttgg | 240 |
| tgaggtaacg | gctcaccaag | ccaacgatga | gtagccgacc | tgagagggtg atcggccaca | 300 |
| ttgggactga | gacacggccc | agactcctac | gggaggcagc | agtggggaat attgcgcaat | 360 |
| gggggaaacc | ctgacgcagc | aacgccgcgt | gagcgatgaa | ggttttcgga tcgtaaagct | 420 |
| ctgtctttgg | ggaagataat | gacggtaccc | aaggaggaag | ctccggctaa ctacgtgcca | 480 |
| gcagccgcgg | taatacgtag | ggagcaagcg | ttgtccggat | tcactgggcg taaagagcac | 540 |
| gtaggcggtt | aattaagtca | ggtgtgaaag | ttttcggctc | aaccggaaaa gtgcacttga | 600 |
| aactggataa | cttgagtatc | ggagaggtaa | gcggaattcc | tagtgtagcg gtgaaatgcg | 660 |
| tagagattag | gaagaacacc | ggtggcgaag | gcggcttact | ggacgataac tgacgctgag | 720 |
| gtgcgaaagc | gtggggagcg | aacaggatta | gataccctgg | tagtccacgc cgtaaacgat | 780 |
| gaatactagg | tgttggggta | actcagtgcc | gcagttaaca | cattaagtat tccgcctggg | 840 |
| gagtacgctc | gcaagagtga | aactcaaagg | aattgacggg | ggcccgcaca agcagcggag | 900 |
| catgtggttt | aattcgaagc | aacgcgaaga | accttaccag | gtcttgacat cccttgaccg | 960 |
| cctaagagat | taggctttcc | ttcgggacaa | ggagacaggt | ggtgcatggt tgtcgtcagc | 1020 |
| tcgtgtcgtg | agatgttggg | ttaagtcccg | caacgagcgc | aacccttatg tttagttact | 1080 |
| aacattcagt | tgaggactct | agacagactg | cccttgaaag | agggaggaag gtgggacga | 1140 |
| cgtcaaatca | tcatgcccct | tacgacctgg | gctacacacg | tgctacaatg gtctgtacag | 1200 |
| agggttgcga | agcagtgatg | ctaagctaat | ctcaaaaagc | agatctcagt tcggattgca | 1260 |
| ggctgcaact | cgcctgcatg | aagtcggagt | tgctagtaat | cgcgaatcag aatgtcgcgg | 1320 |
| tgaatgcgtt | cccgggcctt | gtacacaccg | cccgtcacac | cacgagagtt ggtaacaccc | 1380 |
| gaagccagtg | agctaaccat | taggaggcag | ctgtcgaagg | tggga | 1425 |

<210> SEQ ID NO 5
<211> LENGTH: 1380
<212> TYPE: DNA
<213> ORGANISM: Artificial Sequence
<220> FEATURE:
<223> OTHER INFORMATION: Collinsella shenzhenensis TF06-26 16S rDNA

<400> SEQUENCE: 5

| | | | | |
|---|---|---|---|---|
| cggcacccct | ctccggaggg | aagcgagtgg | cgaacggctg | agtaacacgt ggagaacctg | 60 |
| cccccctcccc | cgggatagcc | gcccgaaagg | acgggtaata | ccggataccc cggggtgccg | 120 |
| catggcaccc | cggctaaagc | cccgacggga | ggggatggct | ccgcggccca tcaggtagac | 180 |
| ggcggggtga | cggcccaccg | tgccgacaac | gggtagccgg | gttgagagac cgaccggcca | 240 |
| gattgggact | gagacacggc | ccagactcct | acggaggca | gcagtgggga atcttgcgca | 300 |
| atgggggga | ccctgacgca | gcgacgccgc | gtgcgggacg | gaggccttcg ggtcgtaaac | 360 |

```
cgctttcagc agggaagagt caagactgta cctgcagaag aagccccggc taactacgtg    420
ccagcagccg cggtaatacg tagggggcga gcgttatccg gattcattgg gcgtaaagcg    480
cgcgtaggcg gcccggcagg ccggggtcg aagcgggggg ctcaacccc cgaagccccc     540 ggaacctccg cggcttgggt ccggtagggg agggtgaac cccggtgta gcggtggaat     600 gcgcagatat cgggtggaac accggtggcg aaggcggccc tctgggccga ccgacgct      660 gaggcgcgaa agctgggga gcgaacagga ttagataccc tggtagtccc agccgtaaac    720
gatggacgct aggtgtgggg ggacgatccc cccgtgccgc agccaacgca ttaagcgtcc   780
cgcctgggga gtacggccgc aaggctaaaa ctcaaaggaa ttgacggggg cccgcacaag   840
cagcggagca tgtggcttaa ttcgaagcaa cgcgaagaac cttaccaggg cttgacatat   900
gggtgaagcg gggagaccc cgtggccgag aggagcccat acaggtggtg catgctgtc    960 gtcagctcgt gtcgtgagat gttgggttaa gtcccgcaac gagcgcaacc cccgccgcgt   1020
gttgccatcg ggtgatgccg ggaacccacg cgggaccgcc gccgtcaagg cggaggaggg   1080
cggggacgac gtcaagtcat catgcccctt atgccctggg ctgcacacgt gctacaatgg   1140
ccggtacaga gggatgccac cccgcgaggg ggagcggatc ccggaaagcc ggccccagtt   1200
cggattgggg gctgcaaccc gccccatga agtcggagtt gctagtaatc gcggatcagc    1260
atgccgcggt gaatgcgttc ccgggccttg tacacaccgc ccgtcacacc acccgagtcg   1320
tctgcacccg aagtcgccgg cccaaccgag agggggagg cgccgaaggt gtggagggtg    1380
```

<210> SEQ ID NO 6  
<211> LENGTH: 1400  
<212> TYPE: DNA  
<213> ORGANISM: Artificial Sequence  
<220> FEATURE:  
<223> OTHER INFORMATION: Lactobacillus gasseri TF08-1 16S rDNA

<400> SEQUENCE: 6

```
ggtgcttgca ccagatgaaa ctagatacaa gcgagcggcg gacgggtgag taacacgtgg     60
gtaacctgcc caagagactg ggataacacc tggaaacaga tgctaatacc ggataacaac    120
actagacgca tgtctagagt ttaaaagatg gttctgctat cactcttgga tggacctgcg    180
gtgcattagc tagttggtaa ggtaacggct taccaaggca atgatgcata gccgagttga    240
gagactgatc ggccacattg ggactgagac acggcccaaa ctcctacggg aggcagcagt    300
agggaatctt ccacaatgga cgcaagtctg atggagcaac gccgcgtgag tgaagaaggg    360
tttcggctcg taaagctctg ttggtagtga agaaagatag aggtagtaac tggcctttat    420
ttgacggtaa ttacttagaa agtcacggct aactacgtgc cagcagccgc ggtaatacgt    480
aggtggcaag cgttgtccgg atttattggg cgtaaagcga gtgcaggcgg ttcaataagt    540
ctgatgtgaa agccttcggc tcaaccggag aattgcatca gaaactgttg aacttgagtg    600
cagaagagga gagtggaact ccatgtgtag cggtggaatg cgtagatata tggaagaaca    660
ccagtggcga aggcggctct ctggtctgca actgacgctg aggctcgaaa gcatgggtag    720
cgaacaggat tagataccct ggtagtccat gccgtaaacg atgagtgcta agtgttggga    780
ggtttccgcc tctcagtgct gcagctaacg cattaagcac tccgcctggg gagtacgacc    840
gcaaggttga aactcaaagg aattgacggg ggcccgcaca gcggtggag catgtggttt    900 aattcgaagc aacgcgaaga accttaccag gtcttgacat ccagtgcaaa cctaagagat    960
taggtgttcc cttcggggac gctgagacag gtggtgcatg gctgtcgtca gctcgtgtcg   1020
```

```
tgagatgttg ggttaagtcc cgcaacgagc gcaaccettg tcattagttg ccatcattaa    1080
gttgggcact ctaatgagac tgccggtgac aaaccggagg aaggtgggga tgacgtcaag    1140
tcatcatgcc ccttatgacc tgggctacac acgtgctaca atggacggta caacgagaag   1200
cgaacctgcg aaggcaagcg gatctctgaa agccgttctc agttcggact gtaggctgca    1260
actcgcctac acgaagctgg aatcgctagt aatcgcggat cagcacgccg cggtgaatac    1320
gttcccgggc cttgtacaca ccgcccgtca caccatgaga gtctgtaaca cccaaagccg    1380
gtgggataac ctttatagga                                                1400

<210> SEQ ID NO 7
<211> LENGTH: 1380
<212> TYPE: DNA
<213> ORGANISM: Artificial Sequence
<220> FEATURE:
<223> OTHER INFORMATION: Lactobacillus acidophilus AM13-1 16S rDNA

<400> SEQUENCE: 7
tgcctaatac atgcaagtcg agcgagctga accaacagat tcacttcggt gatgacgttg     60
ggaacgcgag cggcggatgg gtgagtaaca cgtggggaac ctgccccata gtctgggata    120
ccacttggaa acaggtgcta ataccggata agaaagcaga tcgcatgatc agcttataaa    180
aggcggcgta agctgtcgct atgggatggc cccgcggtgc attagctagt tggtagggta    240
acggcctacc aaggcaatga tgcatagccg agttgagaga ctgatcggcc acattgggac    300
tgagacacgg cccaaactcc tacgggaggc agcagtaggg aatcttccac aatggacgaa    360
agtctgatgg agcaacgccg cgtgagtgaa gaaggttttc ggatcgtaaa gctctgttgt    420
tggtgaagaa ggatagaggt agtaactggc ctttatttga cggtaatcaa ccagaaagtc    480
acggctaact acgtgccagc agccgcggta atacgtaggt ggcaagcgtt gtccggattt    540
attgggcgta aagcgagcgc aggcggaaga ataagtctga tgtgaaagcc ctcggcttaa    600
ccgaggaact gcatcggaaa ctgttttttct tgagtgcaga agaggagagt ggaactccat    660
gtgtagcggt ggaatgcgta gatatatgga agaacaccag tggcgaaggc ggctctctgg    720
tctgcaactg acgctgaggc tcgaaagcat gggtagcgaa caggattaga taccctggta    780
gtccatgccg taaacgatga gtgctaagtg ttgggaggtt tccgcctctc agtgctgcag    840
ctaacgcatt aagcactccg cctggggagt acgaccgcaa ggttgaaact caaaggaatt    900
gacgggggcc cgcacaagcg gtggagcatg tggtttaatt cgaagcaacg cgaagaacct    960
taccaggtct tgacatctag tgcaatccgt agagatacgg agttccette ggggacacta   1020 agacaggtgg tgcatggctg tcgtcagctc gtgtcgtgag atgttgggtt aagtcccgca   1080
acgagcgcaa cccttgtcat tagttgccag cattaagttg ggcactctaa tgagactgcc   1140
ggtgacaaac cggaggaagg tggggatgac gtcaagtcat catgcccctt atgacctggg   1200
ctacacacgt gctacaatgg acagtacaac gaggagcaag cctgcgaagg caagcgaatc   1260
tcttaaagct gttctcagtt cggactgcag tctgcaactc gactgcacga agctggaatc   1320
gctagtaatc gcggatcagc acgccgcggt gaatacgttc ccgggccttg tacacaccgc   1380
```

COMPOSITION AND USES THEREOF

CROSS-REFERENCE TO RELATED APPLICATION

This Application is a Section 371 National Stage Application of International Application No. PCT/CN2018/089319, filed May 31, 2018 and published as WO2019/227418 A1 on Dec. 5, 2019, in Chinese, the content of which is hereby incorporated by reference in its entirety.

FIELD

This application relates to the field of microbial preparations, in particular to microbe or microbe-related composition and use thereof.

BACKGROUND

Ulcerative colitis (UC) and Crohn's disease (CD) are two types of inflammatory bowel disease (IBD), in which IBD is a chronic intestinal inflammatory disease with unknown pathogenesis. Among them, the inflammation of ulcerative colitis mainly occurs in colon and rectum, especially in colon mucosa and submucosa. At present, pathological studies reveal that ulcerative colitis is mainly related to susceptibility genes, mucosal immunity, and intestinal microbes, with clinicopathological manifestations including persistent abdominal pain, diarrhea, or fecal occult blood, as well as repeated illness. With the improvement of living standards and changes in diet, the incidence of ulcerative colitis is on the rise.

The clinical treatment on ulcerative colitis lacks specificity and pertinence due to the unclear pathological mechanism. There are basically three clinical means to treat ulcerative colitis, including nutritional therapy, surgical therapy, and medicine therapy, with the medicine therapy being most important. Clinically, the main medicines for UC are salicylic acids, adrenal glucocorticoids, and immunosuppressive agents, all of which can alleviate UC to a certain extent, but also existing shortages.

Salicylic acids are capable of effectively inhibiting prostaglandin synthesis and scavenging oxygen free radicals, so as to achieve the purpose of alleviating inflammatory response, whereas they can only alleviate inflammation in a short time period and cannot cure the UC disease. For the clinical treatment of ulcerative colitis (UC), the commonly used western medicine of salicylic acids is sulfasalazine (SASP), mainly directing mild, moderate or chronic UC patients. However, salicylic acids have side effects for example generating gastrointestinal reactions, headache, increased reticulocytes, sperm reduction, rash caused by allergic reaction, liver toxicity, leukopenia, anemia or the like, as well as easily caused bacterial flora disorders and enhanced drug resistance due to antibacterial effects of such drugs.

Adrenal glucocorticoids are preferred for severe or paroxysmal UC patients, typically betamethasone. However, adrenal glucocorticoids can cause side effects such as metabolic disorders, retention of water or the like, which can only be useful as emergency medicine and cannot be administered for a long time.

Immunosuppressive agents, such as cyclosporine, can affect the progress of immune response by inhibiting the generation of T cell IL-2, thereby inhibiting ulcerative colitis (UC). However, immunosuppressive therapy is highly drug-dependent and need a long treatment cycle, which is likely to cause nephrotoxicity and secondary infection, thus can only be used as an adjuvant therapy.

Therefore, there is no safe and effective medicament for the treatment of inflammation-related diseases, especially ulcerative colitis.

SUMMARY

The object of the present application is to provide a composition and use thereof. This application proposed the following technical solutions.

In an aspect of the present application, provided in embodiments is a composition, including *Megamonas funiformis* and/or a metabolite thereof, and *Anaerofustis stercorihominis* and/or a metabolite thereof.

It should be noted that a critical point of present application lies in that researches found that the combined administration of *Megamonas funiformis* and *Anaerofustis stercorihominis* is capable of preventing or treating inflammation or inflammation-related diseases, especially effectively preventing or treating ulcerative colitis. Researches reveal that the preventing or treating effects are generated by the reason that (1) *Megamonas funiformis* and *Anaerofustis stercorihominis* can improve the intestinal microecology in the human body, forming a microecology-protective barrier composed of beneficial bacteria, thereby exhibiting efficacy on preventing or treating inflammation or inflammation-related diseases and (2) metabolites generated by *Megamonas funiformis* and *Anaerofustis stercorihominis* can be served as probiotic materials, which promote the prevention or treatment on inflammation or inflammation-related diseases. Therefore, an important purpose of the composition proposed in the present application is for preventing or treating inflammation or inflammation-related diseases, especially for ulcerative colitis or related diseases thereof.

It should also be noted that, in one embodiment, the composition including *Megamonas funiformis* and *Anaerofustis stercorihominis* can form a microecology-protective barrier composed of beneficial bacteria because of the improvement on human intestinal microecology by these two kinds of bacteria, thereby exhibiting efficacy on preventing or treating ulcerative colitis. It can be understood that the improvement on human intestinal microecology can allow preventing or treating effects on not only ulcerative colitis, but also other diseases related to intestinal microecology such as common enteritis, gastritis, or the like. Therefore, the composition proposed in the present application can be useful in preventing or treating inflammation or inflammation-related diseases.

Preferably, the *Megamonas funiformis* is *Megamonas funiformis* AF24-28AC with a deposit number of GDMCC 60093, and the *Anaerofustis stercorihominis* is *Anaerofustis stercorihominis* AM25-6 with a deposit number of GDMCC 60087.

It should be noted that a critical point of the present application lies in that researches found that the combined administration of *Megamonas funiformis* and *Anaerofustis stercorihominis* is capable of preventing or treating inflammation or inflammation-related diseases, in which *Megamonas funiformis* AF24-28AC and *Anaerofustis stercorihominis* AM25-6 are two strains of the most effective bacteria discovered during the research, thus such two strains are further deposited separately. It can be understood that, on the one hand, other strains belonging to the *Megamonas funiformis* species or the *Anaerofustis stercorihominis* species capable of reaching or even exceeding the efficacy achieved by the combination of *Megamonas funiformis* AF24-28AC and *Anaerofustis stercorihominis* AM25-6 can also be applied within the concept of the present application. On the other hand, other strains belonging to the *Megamonas funiformis* species or the *Anaerofustis stercorihominis* species, which cannot reach the efficacy achieved by the combination of *Megamonas funiformis* AF24-28AC and *Anaerofustis stercorihominis* AM25-6 can also be applied within the concept of the present application.

Preferably, the composition further includes *Collinsella shenzhenensis* and/or a metabolite thereof.

Preferably, the *Collinsella shenzhenensis* is *Collinsella shenzhenensis* TF06-26 with a deposit number of GDMCC 60090.

Preferably, the composition further includes *Roseburia inulinivorans* and/or a metabolite thereof.

Preferably, the *Roseburia inulinivorans* is *Roseburia inulinivorans* DSM 16841 with a deposit number of DSM 16841.

Preferably, the composition further includes *Butyribacter intestini* and/or a metabolite thereof.

Preferably, the *Butyribacter intestini* is *Butyribacter intestini* TF01-11 with a deposit number of CGMCC 10984.

Preferably, the composition further includes *Lactobacillus gasseri* and/or a metabolite thereof and *Lactobacillus acidophilus* and/or a metabolite thereof.

Preferably, the *Lactobacillus gasseri* is *Lactobacillus gasseri* TF08-1 with a deposit number of GDMCC 60092 and the *Lactobacillus acidophilus* is *Lactobacillus acidophilus* AM13-1 with a deposit number of GDMCC 60091.

It should be noted that, the research of the present application has demonstrated not only that the combined administration of *Megamonas funiformis* and *Anaerofustis stercorihominis* is capable of preventing or treating inflammation or inflammation-related diseases, but also that *Collinsella shenzhenensis, Roseburia inulinivorans* or *Butyribacter intestini* can also be included in the composition or *Lactobacillus gasseri* and *Lactobacillus acidophilus* can also be included in the composition without affecting the efficacy of the combined *Megamonas funiformis* and *Anaerofustis stercorihominis*. The combination schemes described above are all sufficient to prevent or treat inflammation or inflammation-related diseases.

Preferably, the composition further includes probiotics and/or prebiotics.

It should be noted that, the critical point of the present application lies in that the combined administration of *Megamonas funiformis* and *Anaerofustis stercorihominis* is capable of preventing or treating inflammation or inflammation-related diseases. It can be understood that probiotics or prebiotics may be added into the composition without affecting the efficacy of the combined *Megamonas funiformis* and *Anaerofustis stercorihominis*, such that the composition can have more functions or strengthened efficacy. These probiotics or prebiotics can be probiotics or prebiotics reported in existing studies, which is not specifically limited herein.

Preferably, in an embodiment, the prebiotics are at least one selected from the group consisting of fructooligosaccharide (FOS), galactooligosaccharide (GOS), xylooligosaccharide (XOS), lactosucrose (LACT), soybean oligosaccharide (SOS), inulin and oligosaccharide.

Preferably, the composition further includes a substance capable of maintaining the viability of at least one of the bacteria.

It can be understood that, in order to maintain the viability of individual bacterial strains in the composition and ensure the efficacy thereof, various substances capable of maintaining the viability of the bacterial strains can also be added into the composition. These substances as described above can be those substances maintaining viability reported in existing studies, which is not specifically limited herein.

Preferably, in an embodiment, the substance capable of maintaining the viability of at least one of the bacteria is at least one selected from the group consisting of cysteine, glutathione, butylated hydroxyanisole, dibutyl methyl toluene, tocopherol, antioxidant of bamboo leaves, D-isoascorbic acid or a sodium salt thereof, sodium ascorbate, calcium ascorbate, phospholipid, Vitamin C and Vitamin E.

Preferably, the composition further includes a pharmaceutically or food acceptable carrier or excipient.

It should be noted that, the composition of the present application has the efficacy of preventing or treating inflammation or inflammation-related diseases. In one embodiment, the preventing or treating effects are achieved mainly by orally administering the composition. Therefore, the composition may also include a pharmaceutically or food acceptable carrier or excipient for use convenience.

Preferably, the pharmaceutically or food acceptable carrier or excipient is at least one selected from glucose, lactose, sucrose, starch, mannitol, dextrin, glycerin fatty acid ester, polyethylene glycol, hydroxyethyl starch, ethylene glycol, polyoxyethylene sorbitol fatty acid ester, amino acid, gelatin, albumin, water and saline.

In another aspect, provided in embodiments is use of the composition in the manufacture of a food, a health product, a food additive, or a medicament for treating or preventing inflammation or inflammation-related diseases.

It can be understood that the composition of the present application has the efficacy of preventing or treating inflammation or inflammation-related diseases. For use convenience, the composition can be prepared into foods, health products, food additives or medicines.

Preferably, the composition can especially be useful in the manufacture of a food, a health product, a food additive, or a medicament for treating or preventing ulcerative colitis or related diseases.

In a further aspect, provided in embodiments is use of the composition in the manufacture of a food, a health product, a food additive, or a medicament for controlling weight loss in a mammal.

The weight loss in a mammal is especially caused by inflammation.

Preferably, the inflammation is ulcerative colitis. That is, weight loss in a mammal caused by ulcerative colitis is controlled.

In a furthermore aspect, provided in embodiments is use of the composition in the manufacture of a food, a health product, a food additive, or a medicament for reducing a disease activity index of a mammal.

In a furthermore aspect, provided in embodiments is use of the composition in the manufacture of a food, a health product, a food additive, or a medicament for relieving intestinal lesion of a mammal.

It should be noted that, the efficacy of preventing or treating inflammation or inflammation-related diseases by the present composition is mainly reflected in controlling the weight loss caused by inflammation or inflammation-related diseases, reducing the disease activity index caused by inflammation or inflammation-related diseases and relieving intestinal lesion of the mammal. Therefore, the composition of the present application can also be used alone to prepare foods, health products, food additives or medicines for controlling weight loss of a mammal, reducing the disease activity index of a mammal or relieving intestinal lesion of a mammal.

In a furthermore aspect, provided in embodiments is a method for treating or preventing inflammation or inflammation-related diseases comprising administering the composition.

In a furthermore aspect, provided in embodiments is a method for controlling weight loss in a mammal comprising administering the composition.

In a furthermore aspect, provided in embodiments is a method for reducing a disease activity index of a mammal comprising administering the composition.

In a furthermore aspect, provided in embodiments is a method for relieving intestinal lesion of a mammal comprising administering the composition.

It should be noted that, in the various methods described above, the composition is mainly orally administered to treat or prevent inflammation or inflammation-related diseases, control weight loss in a mammal, reduce the disease activity index of a mammal or relieve intestinal lesion of a mammal.

In a furthermore aspect, provided in embodiments is a food including the composition.

Preferably, the food is a lactic acid drink or a soybean milk drink. The food in the present application broadly refers to an edible article in any form, which is not limited to the lactic acid drink or the soybean milk drink. For example, the food may also be fermented foods, animal feeds or the like.

It should be noted that, the food described above contains the composition of the present application, thus also capable of exhibiting effects on treating or preventing inflammation or inflammation-related diseases, controlling weight loss in a mammal, reducing the disease activity index of a mammal and relieving intestinal lesion of a mammal. It can be understood that, the key to the food of the present application is the composition of the present application contained in it, and the specific form such as solid, liquid or the like may be determined according to different food products or usage requirements which is not specifically limited herein. In an embodiment, the composition of the present application is mainly made into common lactic acid drinks or soybean milk drinks for convenient drinking. The composition of the present application may be made into solid foods such as milk slices, cheese bars or the like, which is not specifically limited herein.

It should also be noted that, the amount of active *Megamonas funiformis* and *Anaerofustis stercorihominis* contained in the food or the administration dosage thereof is not specifically limited herein, which can be flexibly selected according to actual needs in practice. Taking the *Megamonas funiformis* AF24-28AC and the *Anaerofustis stercorihominis* AM25-6 as examples, the research of this application shows that an excellent treatment effect on ulcerative colitis can be achieved when the administration dosage of the composition is 0.2 mL per day, in which the concentration of the *Megamonas funiformis* AF24-28AC and the *Anaerofustis stercorihominis* AM25-6 in the composition is $10^9$ cfu/mL. Such a bacterial concentration or the administration dosage may be served as a reference usage amount or a reference administration dosage for food, health products, food additives or medicines, respectively.

In a furthermore aspect, provided in embodiments is a health product comprising the composition.

It should be noted that, the health product described above contains the composition of the present application, thus also capable of exhibiting effects on treating or preventing inflammation or inflammation-related diseases, controlling weight loss in a mammal, reducing the disease activity index of a mammal and relieving intestinal lesion of a mammal.

In a furthermore aspect, provided in embodiments is a food additive comprising the composition.

It should be noted that, the composition of the present application can be eaten in combination with common food materials. For example, the common food materials include cereals and potatoes, in which the cereals include rice, noodle and miscellaneous grains and the potatoes include potato (*Solanum tuberosum*), sweet potato (*Ipomoea batatas*) or the like; animal foods, including meat, poultry, fish, milk, eggs or the like; beans and products thereof, including soybean and other dried beans; vegetables and fruits, including fresh beans, rhizomes, leafy vegetables, solanaceous vegetables or the like; foods purely producing heat energy, including animal or vegetable oils, starches, edible sugars, alcohols or the like. Therefore, the composition of the present application can be served as a food additive, or a modifier alone to be added into various food materials for direct usage, thus exhibiting effects on treating or preventing inflammation or inflammation-related diseases.

In a furthermore aspect, provided in embodiments is a medicament comprising the composition.

Preferably, the medicament is in a form of tablets, granules, powders, an enteric-coated agent, solutions, or suspension.

It should be noted that, the medicament described above contains the composition of the present application, thus capable of exhibiting effects on treating or preventing inflammation or inflammation-related diseases. The medicament of this application may contain a single composition or may be combined with other anti-inflammatory agents as long as these agents do not affect the activity of each other. It can be understood that the medicament of the present application may have various existing dosage forms as long as the activity of each strain of the composition in the medicament is not affected. Further, the medicament of the present application may include excipients commonly useful in medicine or dosage forms, such as stabilizers, wetting agents, emulsifiers, adhesives, isotonic agents, or the like.

The medicament of the present application may be administered in any form selected from oral liquid, tablet, injection, orally disintegrating tablet, lyophilized powder preparation and enteric-coated agent. Preferably, the medicament is an enteric-coated agent, such as an enteric-coated capsule or an enteric-coated tablet, so as to ensure the active ingredient of the medicament (i.e., bacteria components) capable of passing through stomach smoothly without being destroyed by gastric acid. More preferably, the medicament is an enteric-coated tablet for oral usage.

The enteric-coated agent in this application refers to a pharmaceutical dosage form that does not disintegrate in gastric juice but can be disintegrated and absorbed in intestinal juice. The enteric-coated agent includes an enteric-coated capsule or an enteric-coated tablet. The enteric-coated capsule is formed by encapsulating a powdered medicine in a capsule shell allowed for common medicines. The enteric-coated tablet is formed by wrapping an enteric coating on the surface of common medicines in the tablet form. The "enteric coating" in this application is abbreviated as "coating", and includes all the coatings allowed for common medicines which would not be degraded by gastric acid but can be fully decomposed in small intestine and quickly release the medicament of this application. For example, the coating of the present application can be maintained at 36 to 38° C. for more than 2 hours in a synthetic gastric acid such as a hydrochloric acid solution of pH=1, preferably decomposed within 1 hour in a synthetic intestinal juice such as a buffer solution of pH=7.0.

Preferably, the thickness of enteric coating of the enteric-coated tablet is 5 to 100 μm, preferably 20 to 80 μm. The ingredients of the enteric coating are selected from known conventional materials.

The amount of various active bacteria contained in the composition of the medicament of the present application or the administration dosage thereof is not particularly limited, which can be flexibly selected according to health conditions of the subject to be administered in practice. The research of this application shows that an excellent treatment effect on ulcerative colitis can be achieved when the administration dosage of the composition is 0.2 mL per day, in which the concentration of the *Megamonas funiformis* AF24-28AC and the *Anaerofustis stercorihominis* AM25-6 in the composition is $10^9$ cfu/mL. Such a bacterial concentration or the administration dosage may be served as a reference usage amount for medicament.

The application achieved the following beneficial effects.

The composition of the present application, by including the combination of *Megamonas funiformis* and *Anaerofustis stercorihominis*, can exhibit excellent efficacy on preventing or treating inflammation or inflammation-related diseases, especially ulcerative colitis. Thus, the present application provides a new composition which is safe and effective, has low toxic and side effect and does not easily develop resistance.

Figure 1:
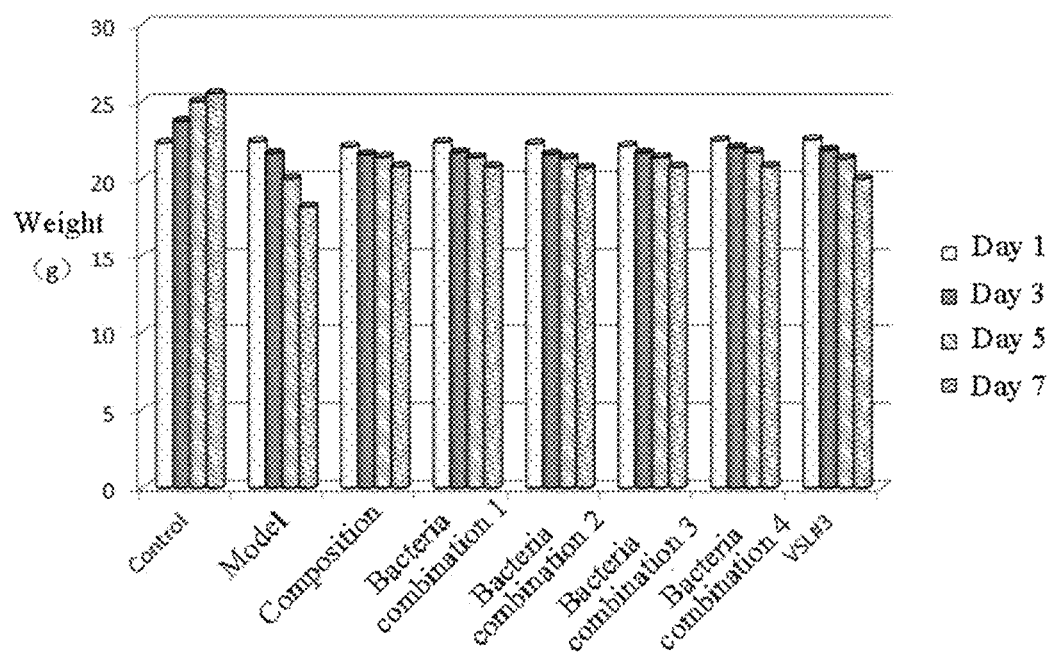
FIG. 1 is a graph showing the change of weight of mice in a control group, a model group, a VSL[#]3 group, a composition treatment group, a bacteria combination 1 treatment group, a bacteria combination 2 treatment group, a bacteria combination 3 treatment group or a bacteria combination 4 treatment group in examples of this application.

The *Megamonas funiformis* AF24-28AC of this application is deposited in the Guangdong Microbial Culture Collection Center on Oct. 13, 2016, with a deposit number of GDMCC 60093. The depository is located at the fifth floor of the Experimental Building of the Guangdong Institute of Microbiology, No. 100 Xianlie Zhong Road, Guangzhou, Guangdong, PR China.

The *Anaerofustis stercorihominis* AM25-6 of this application is deposited in the Guangdong Microbial Culture Collection Center on Oct. 13, 2016, with a deposit number of GDMCC 60087. The depository is located at the fifth floor of the Experimental Building of the Guangdong Institute of Microbiology, No. 100 Xianlie Zhong Road, Guangzhou, Guangdong, PR China.

The *Collinsella shenzhenensis* TF06-26 of this application is deposited in the Guangdong Microbial Culture Collection Center on Oct. 13, 2016, with a deposit number of GDMCC 60090. The depository is located at the fifth floor of the Experimental Building of the Guangdong Institute of Microbiology, No. 100 Xianlie Zhong Road, Guangzhou, Guangdong, PR China.

The *Roseburia inulinivorans* DSM 16841 with a deposit number of DSM 16841 is purchased from the German Collection of Microorganisms and Cell Cultures (DSMZ) at Braunschweig, GERMANY.

The *Butyribacter intestini* TF01-11 of this application is deposited in the China General Microbiological Culture Collection Center on Jun. 16, 2015, with a deposit number of CGMCC 10984. The depository is located at the Institute of Microbiology, Chinese Academy of Sciences, No. 3, Park 1, Beichen West Road, Chaoyang District, Beijing.

The *Lactobacillus gasseri* TF08-1 of this application is deposited in the Guangdong Microbial Culture Collection Center on Oct. 13, 2016, with a deposit number of GDMCC 60092. The depository is located at the fifth floor of the Experimental Building of the Guangdong Institute of Microbiology, No. 100 Xianlie Zhong Road, Guangzhou, Guangdong, PR China.

The *Lactobacillus acidophilus* AM13-1 of this application is deposited in the Guangdong Microbial Culture Collection Center on Oct. 13, 2016, with a deposit number of GDMCC 60091. The depository is located at the fifth floor of the Experimental Building of the Guangdong Institute of Microbiology, No. 100 Xianlie Zhong Road, Guangzhou, Guangdong, PR China.

DETAILED DESCRIPTION

With the in-depth study of intestinal microecology, it has been found that the onset of ulcerative colitis is closely related to the composition of intestinal microbes. The imbalance of intestinal bacteria is closely related to the inflammation in the intestinal mucosa, in which the excessive proliferation of harmful bacteria can trigger the inflammation, thus induce the onset of ulcerative colitis. There are large numbers of beneficial bacteria in a healthy human intestine, and these beneficial bacteria constitute the first biological barrier of the intestine.

Based on the above research and knowledge, this application develops and proposes a new composition, which includes *Megamonas funiformis* and/or a metabolite thereof and *Anaerofustis stercorihominis* and/or a metabolite thereof. The composition of the present application can have effects on preventing or treating not only ulcerative colitis, but also other diseases related to intestinal microecology such as common enteritis, gastritis, or the like. Therefore, the composition proposed in the present application can be useful in preventing or treating inflammation or inflammation-related diseases.

According to one embodiment, the composition including *Megamonas funiformis* AF24-28AC with a deposit number of GDMCC 60093 and *Anaerofustis stercorihominis* AM25-6 with a deposit number of GDMCC 60087 has a better treatment effect on ulcerative colitis than that of the VSL[#]3 probiotics compound produced by ALFASIGMA company, USA, indicating that the present composition can be useful in the manufacture of a food, a health product, a food additive, or a medicament for treating or preventing inflammation or inflammation-related diseases.

The application will be further described in detail below through specific examples. The following examples only further illustrate the present application and should not be construed as limiting the present application.

Example 1

In this example, a mouse model of ulcerative colitis induced by dextran sulfate sodium (abbreviated as DSS)

with a molecular weight of 36000-50000 Da was used as the subject to be researched to study the treatment effect of the composition including *Megamonas funiformis* AF24-28AC and *Anaerofustis stercorihominis* AM25-6 on ulcerative colitis. Further, this composition of *Megamonas funiformis* AF24-28AC and *Anaerofustis stercorihominis* AM25-6 is applied in combination with various probiotics. The probiotics to be added include *Collinsella shenzhenensis* TF06-26, *Roseburia inulinivorans* DSM 16841, *Butyribacter intestini* TF01-11, *Lactobacillus gasseri* TF08-1 and *Lactobacillus acidophilus* AM13-1. The example is described in detail as follows.

1. Materials and Methods
   1.1 Cultivation and Identification of Strains
   1.1.1 *Megamonas funiformis* AF24-28AC The *Megamonas funiformis* AF24-28AC in this example was cultured using peptone yeast extract glucose (PYG) medium under anaerobic conditions at 37° C. The colonies of the AF24-28AC strain after cultured in the PYG medium for 2 days are light yellow and flat, with irregular wavy edges, has low water content and about 2-3 mm of diameter. The microscopic morphology of the bacterium is rod-shaped, gram-negative, and does not produce spores and flagella. The *Megamonas funiformis* AF24-28AC is deposited in the Guangdong Microbial Culture Collection Center, with a deposit number of GDMCC 60093.

The specific steps of isolation and identification of *Megamonas funiformis* AF24-28AC are as follows.

1.1.1.1 Separation and Cultivation of Strain

A sample was obtained from feces of a healthy female. Strains were separated by a gradient dilution spreading method. The culture medium was the PYG medium purchased from HUANKAI Microbial Technology Company for anaerobic culture. The anaerobic gas component was $N_2:CO_2:H_2=90:5:5$. After culture for 48 hours, a single colony was picked out and streaked in culture medium for strain isolation, thus obtaining a pure culture of single bacterium.

1.1.1.2 16S rDNA Identification of Strain

The genomic DNA of individual isolated strain was extracted, followed by PCR amplification via using the 16S rDNA universal primers. The 16S rDNA amplified product was subjected to electrophoresis detection, purifying and sequencing in a 3730 sequencer to obtain the 16S rDNA sequence of corresponding strain. After that, the 16S rDNA sequence obtained was aligned to the EZBio Cloud database for identification of strain.

The PCR amplification system for 16S rDNA sequence includes 10×PCR buffer 3 μL, dNTPs 2.5 μL, an upstream primer 27F 0.5 μL, a downstream primer 1492R 0.5 μL, Taq enzyme 0.3 μL, a template 1 μL and ddH$_2$O 18.2 μL.

The amplification condition for 16S rDNA sequence is as follows.

| | | |
|---|---|---|
| 94° C. | 4 minutes | |
| 94° C. | 30 seconds | |
| 65° C.-57° C. | 40 seconds | } 20 cycles |
| 72° C. | 90 seconds | |
| 94° C. | 30 seconds | |
| 57° C. | 40 seconds | } 10 cycles |
| 72° C. | 90 seconds | |
| 72° C. | 10 minutes | |
| 4° C. | ∞ | |

Among the amplification conditions, "65° C.-57° C. for 40 seconds" means that the temperature decreases proportionally after each cycle, more specific, the annealing temperature in the first cycle is 65° C. and the annealing temperature decreases to 57° C. in the 20th cycle.

The upstream primer of the 16S rDNA universal primers in this example is primer 27f which is of the sequence of SEQ ID NO. 1.

The downstream primer of the 16S rDNA universal primers is primer 1492r which is of the sequence of SEQ ID NO. 2.

```
SEQ ID NO. 1:
5'-AGAGTTTGATCATGGCTCAG-3'

SEQ ID NO. 2:
5'-TAGGGTTACCTTGTTACGACTT-3'
```

The obtained 16S rDNA sequence of the isolated strain AF24-28AC is of the sequence of SEQ ID NO. 3. The alignment results via EZBio Cloud database showed that the AF24-28AC strain isolated in this example has the highest homology with *Megamonas funiformis* DSM 19343 purchased from the German Collection of Microorganisms and Cell Cultures, with a similarity of 99.09%. Thus, the AF24-28AC strain was determined to belong to *Megamonas funiformis* species, named as *Megamonas funiformis* AF24-28AC and deposited.

1.1.2 *Anaerofustis stercorihominis* AM25-6

The *Anaerofustis stercorihominis* AM25-6 in this example was cultured using peptone yeast extract glucose (PYG) medium under anaerobic conditions at 37° C. The colonies of the AM25-6 strain after cultured in PYG medium for 2 days are light yellow and needle-shaped, with small size of colony and has about 0.5 mm of diameter. The microscopic morphology of the bacterium is short rod-shaped, gram-positive, and does not produce spores and flagella. The *Anaerofustis stercorihominis* AM25-6 is deposited in the Guangdong Microbial Culture Collection Center, with a deposit number of GDMCC 60087.

The specific steps of isolation and identification of *Anaerofustis stercorihominis* AM25-6 are as follows.

1.1.2.1 Separation and Cultivation of Strain

A sample was collected from feces of a healthy male, followed by transferred into a sterile sample tube and brought back to the laboratory for sorting within 1 hour. The collected fresh sample was immediately transferred to an anaerobic operation box, after which 0.2 g of the sample was suspended in 1 mL of sterile phosphate buffered saline (abbreviated as PBS), shaken and mixed thoroughly. Strains were separated by a gradient dilution spreading method. The culture medium was the PYG medium purchased from HUANKAI Microbial Technology Company. The coated plate was placed at 37° C. for anaerobic culture, in which the anaerobic gas components are $N_2:CO_2:H_2=90:5:5$. After culture for 3 days, a single colony was picked out and streaked in culture medium for strain isolation, thus obtaining a pure culture of single strain. The isolated single strain was further cultured until the concentration of bacterium reached about $10^9$ cfu/mL, and 400 μL of the bacterial liquid was added to 400 μL of 40% glycerol such that the glycerol was in a 20% concentration, then stored at −80° C. of ultra-low temperature.

1.1.2.2 16S rDNA Identification of Strain

The genomic DNA of individual isolated strain was extracted, followed by PCR amplification via using the 16S rDNA universal primers. The 16S rDNA amplified product was subjected to electrophoresis detection, purifying and sequencing in a 3730 sequencer to obtain the 16S rDNA sequence of corresponding strain. After that, the 16S rDNA sequence obtained was aligned to the EZBio Cloud database for identification of strain.

The 16S rDNA universal primers and the PCR amplification system for 16S rDNA sequence are the same as those recited in "1.1.1.2 16S rDNA identification of strain". The amplification condition for 16S rDNA sequence is pre-denaturation at 95° C. for 4 minutes, and then 30 cycles of denaturation at 95° C. for 30 seconds, annealing at 57° C. for 40 seconds and extension at 72° C. for 90 seconds.

The sequenced results showed that the 16S rDNA sequence of the isolated strain AM25-6 is of the sequence of SEQ ID NO. 4. The alignment results via EZBio Cloud database showed that the AM25-6 strain isolated in this example has the highest homology with *Anaerofustis stercorihominis* DSM 17244 purchased from the German Collection of Microorganisms and Cell Cultures, with 99.86% of homology. Thus, the AM25-6 strain was determined to belong to *Anaerofustis stercorihominis* species, named as *Anaerofustis stercorihominis* AM25-6 and deposited.

1.1.3 *Collinsella shenzhenensis* TF06-26

The *Collinsella shenzhenensis* TF06-26 in this example was cultured using peptone yeast extract glucose (PYG) medium under anaerobic conditions at 37° C. The colonies of the TF06-26 strain after cultured in the anaerobic PYG medium for 2 days are white, convex and viscous, and has about 1-2 mm of diameter. The microscopic morphology of the bacterium is short rod-shaped, gram-negative, and does not produce spores and flagella. The *Collinsella shenzhenensis* TF06-26 is deposited in the Guangdong Microbial Culture Collection Center, with a deposit number of GDMCC 60090.

The specific steps of isolation and identification of *Collinsella shenzhenensis* TF06-26 are as follows.

1.1.3.1 Sample Collection

The *Collinsella shenzhenensis* TF06-26 in this experiment was isolated from a feces sample of a healthy young female volunteer in Shenzhen.

1.1.3.2 Preparation of Culture Medium and Phosphate Buffered Saline (PBS)

The culture medium for strain isolation in this experiment was the PYG medium purchased from HUANKAI Microbial Technology Company. The specific components of the PYG medium includes peptone 5 g, tryptic casein 5 g, yeast powder 10 g, beef extract 5 g, glucose 5 g, $K_2HPO_4$ 2 g, TWEEN 80 (i.e., polysorbate 80) 1 mL, Cysteine-HCl.$H_2O$ 0.5 g, hemoglobin 5 mg, vitamin K1 1 μL, inorganic salt solution 40 mL, resazurin 1 mg, distilled water 950 mL, adjusted to 6.8 to 7.0 of pH. Sterilization conditions are autoclave sterilization at 115° C. for 25 minutes. Solid medium was poured onto culture plates in an anaerobic operation box. Among them, 1 L inorganic salt solution includes $CaCl_2.2H_2O$ 0.25 g, $MgSO_4.7H_2O$ 0.5 g, $K_2HPO_4$ 1 g, $KH_2PO_4$ 1 g, $NaHCO_3$ 10 g and NaCl 2 g.

PBS preparation: 8 g of NaCl, 0.2 g of KCl, 3.63 g of $Na_2HPO_4.12H_2O$, 0.24 g of $KH_2PO_4$ and 0.5 g of cysteine hydrochloride weighed were dissolved in 900 mL of double-distilled water, adjusted to 7.4 of pH by using hydrochloric acid and NaOH solution, followed by adding water to a constant volume of 1 L, inflating $N_2$ gas to deoxygenate for 30 seconds, sealing the solution in an anaerobic bottle and autoclaved at 115° C. for 25 minutes, for latter use.

1.1.3.3 Separation of Strain

The collected fresh feces sample was immediately transferred to an anaerobic operation box, after which about 0.2 g of the feces sample was suspended in sterile PBS solution and mixed thoroughly, in which the anaerobic gas components in the anaerobic operation box are $N_2:H_2:CO_2=90:5:5$ (v/v). The suspension solution was diluted in 10-fold gradient, spread onto culture plates containing culture medium, and cultured under anaerobic conditions at 37° C. for 2 days. After culture for 2 days, a single colony was picked out and streaked in culture medium for strain isolation, thus obtaining a pure culture of single strain, then stored at −80° C. for glycerol freeze preservation or for vacuum freeze drying preservation.

1.1.3.4 16S rDNA Identification of Strain

The isolated pure culture strains were subjected to 16S rDNA sequencing to obtain classification information of each strain. The isolated single strain was further cultured in PYG liquid medium for 24 hours until the concentration of bacterium reached about $10^8$ cfu/mL. The genomic DNA of individual isolated strain was extracted, followed by PCR amplification for 16S rDNA sequence via using the genomic DNA as a template. The 16S rDNA amplified product was subjected to electrophoresis detection, purifying and sequencing in a 3730 sequencer to obtain the 16S rDNA sequence of corresponding strain. After that, the 16S rDNA sequence obtained was aligned to the EZBio Cloud database for identification of strain.

The 16S rDNA universal primers and the PCR amplification system for 16S rDNA sequence are the same as those recited in "1.1.1.2 16S rDNA identification of strain". The amplification condition for 16S rDNA sequence are the same as those recited in "1.1.2.2 16S rDNA identification of strain".

The sequencing results showed that the 16S rDNA sequence of the isolated strain TF06-26 is of the sequence of SEQ ID NO. 5. The alignment results via EZBio Cloud database showed that the TF06-26 strain isolated in this example has the highest homology with *Collinsella aerofaciens* JCM 10188 purchased from the Japan Collection of Microorganisms.

1.1.3.5 Physiological and Biochemical Characteristics of TF06-26

The TF06-26 strain is catalase-negative, oxidase-negative and non-motility. For the TF06-26 strain, growth temperature range is 25-45° C., growth pH value range is 5.0-8.0, NaCl tolerance concentration is 2%, and bile salt tolerance concentration is 0.3%. The substrate utilization, API 20A and API 50CHL of the TF06-26 strain and related reference strain *Collinsella aerofaciens* JCM 10188 purchased from the Japan Collection of Microorganisms are shown in Table 1, in which "+" indicates a positive reaction, "−" indicates a negative reaction and "w" indicates a weak positive reaction.

TABLE 1

Substrate utilization of TF06-26 and JCM 10188

| Substrate | TF06-26 | JCM 10188 | Substrate | TF06-26 | JCM 10188 |
|---|---|---|---|---|---|
| API 20A | | | | | |
| Indole production | − | − | Gelatin hydrolysis | − | − |
| Urea (urease) | − | − | esculin | − | − |
| glucose | + | + | glycerinum | − | − |
| Mannitol | − | − | cellobiose | − | − |
| lactose | + | w | mannose | + | + |
| sucrose | − | + | melezitose | − | − |
| maltose | + | + | raffinose | − | − |
| salicyl alcohol | w | − | sorbitol | − | − |
| xylose | − | − | rhamnose | − | − |

TABLE 1-continued

Substrate utilization of TF06-26 and JCM 10188

| Substrate | TF06-26 | JCM 10188 | Substrate | TF06-26 | JCM 10188 |
|---|---|---|---|---|---|
| arabinose | − | − | trehalose | − | − |
| API 50CHL | | | | | |
| glycerinum | − | − | salicyl alcohol | + | − |
| erythritol | − | − | cellose | w | − |
| D-Arabinose | − | − | maltose | + | − |
| L-Arabinose | − | − | lactose | + | w |
| ribose | − | − | melibiose | + | w |
| D-xylose | − | − | sucrose | − | − |
| L-xylose | − | − | trehalose | − | w |
| adonitol | − | − | Inulin | − | − |
| β-methyl-D-xyloside | − | − | melezitose | − | − |
| galactose | + | w | raffinose | − | − |
| glucose | + | + | starch | − | − |
| fructose | + | w | glycogen | − | − |
| mannose | + | w | xylitol | − | − |
| sorbose | − | − | gentiobiose | − | − |
| rhamnose | − | − | D-turanose | − | − |
| dulcitol | − | − | D-lyxose | − | − |
| inositol | − | − | D-tagatose | − | − |
| mannitol | − | − | D-Fucose | + | + |
| sorbitol | − | − | L-Fucose | − | − |
| α-methyl-D-mannoside | − | − | D-arabitol | − | − |
| α-methyl-D-glucoside | − | − | L-arabitol | − | − |
| N-acetyl-glucosamine | + | + | gluconate | − | − |
| amygdalin | − | − | 2-ketone-gluconate | − | w |
| arbutin | w | − | 5-ketone-gluconate | − | − |

The comparison of carbon source utilization of the TF06-26 strain and the JCM 10188 strain in Table 1 shows that the TF06-26 strain and the JCM 10188 strain were significantly different in the utilization of lactose, sucrose, salicyl alcohol, galactose, fructose, mannose, arbutin, cellobiose, maltose, melibiose, trehalose and 2-ketone-gluconate, preliminary indicating that the TF06-26 strain and the JCM 10188 strain belong to different species.

1.1.3.6 Genome Hybridization Test of the New Species TF06-26 and Related Strain JCM 10188

With reference to the 16S rDNA alignment results, it is showed that the TF06-26 strain has the highest homology with *Collinsella aerofaciens* JCM 10188, with a similarity of 99.9%. Further, genome hybridization test was performed to distinguish TF06-26 and JCM 10188 at the species level.

The results of genome hybridization test showed that the homology of TF06-26 and JCM 10188 was 51%. According to "Berger's Bacteria Identification Manual", two strains having a DNA hybridization value higher than 70% can be determined to be the same species. Since the DNA hybridization value of TF06-26 and JCM 10188 is less than 70%, the TF06-26 strain is determined to be a new strain different from the known bacteria. According to the International Bacteria Classification Committee (IBSP) bacterial naming rules, this new strain was named *Collinsella shenzhenensis* sp. nov. The TF06-26 strain (i.e., *Collinsella shenzhenensis* TF06-26) was used as a model strain of this species, which was deposited.

1.1.4 *Roseburia inulinivorans* DSM 16841

The *Roseburia inulinivorans* DSM 16841 in this example was cultured using anaerobic PYG medium under anaerobic conditions at 37° C. The colonies of the DSM 16841 strain after cultured in the anaerobic PYG medium for 2 days are light yellow with a diameter of about 1 mm. The microscopic morphology of the bacterium is short rod-shaped, gram-positive, and does not produce spores and flagella. The *Roseburia inulinivorans* DSM 16841 is purchased from the German Collection of Microorganisms and Cell Cultures (DSMZ), with a deposit number of DSM 16841.

1.1.5 *Butyribacter intestini* TF01-11

The *Butyribacter intestini* TF01-11 in this example was cultured using anaerobic PYG medium under anaerobic conditions at 37° C. The colonies of the TF01-11 strain after cultured in the anaerobic PYG medium for 2 days are off-white, opaque, smooth, with irregular edges like pseudo-roots and has a diameter of about 2 mm. The microscopic morphology of the bacterium through gram staining and microscopic observation, is gram-positive, long rod-shaped, mobile, with flagella and does not produce spores. The bacterium has a diameter of about 0.5-1.0 mm and a length of about 2.0-8.0 mm. The *Butyribacter intestini* TF01-11 is obtained from and deposited in the China General Microbiological Culture Collection Center (CGMCC), with a deposit number of CGMCC 10984.

1.1.6 *Lactobacillus gasseri* TF08-1

The *Lactobacillus gasseri* TF08-1 in this example was cultured using PYG medium under anaerobic conditions at 37° C. The colonies of the TF08-1 strain after cultured in the PYG medium for 2 days are white, low convex, nearly round and with wavy edges, has a diameter of about 1-2 mm. The microscopic morphology of the bacterium is rod-shaped, gram-positive, and does not produce spores and flagella. The *Lactobacillus gasseri* TF08-1 is deposited in the Guangdong Microbial Culture Collection Center, with a deposit number of GDMCC 60092.

The specific steps of isolation and identification of *Lactobacillus gasseri* TF08-1 are as follows.

1.1.6.1 Sample Collection

The *Lactobacillus gasseri* TF08-1 in this experiment was isolated from a feces sample of a 16-year-old healthy female volunteer in Shenzhen, Guangdong. The diet and physical conditions of the volunteer were recorded in detail.

1.1.6.2 Separation and Cultivation of Strain

The culture medium for strain isolation was prepared in advance, in which the culture medium in this experiment was the PYG medium purchased from HUANKAI Microbial Technology Company. The specific components of the PYG medium includes peptone 5 g, tryptic casein 5 g, yeast powder 10 g, beef extract 5 g, glucose 5 g, $K_2HPO_4$ 2 g, TWEEN 80 (i.e., polysorbate 80) 1 mL, Cysteine-$HCl.H_2O$ 0.5 g, sodium sulfide 0.25 g, hemoglobin 5 mg, vitamin $K_1$ 1 µL, inorganic salt solution 40 mL, resazurin 1 mg, distilled water 950 mL, adjusted to 6.8 to 7.0 of pH. Sterilization conditions are autoclave sterilization at 115° C. for 25 minutes. Solid medium was added with 1.5% agar and poured onto culture plates in an anaerobic operation box. 1 L inorganic salt solution includes $CaCl_2.2H_2O$ 0.25 g, $MgSO_4.7H_2O$ 0.5 g, $K_2HPO_4$ 1 g, $KH_2PO_4$ 1 g, $NaHCO_3$ 10 g and NaCl 2 g.

The collected fresh feces sample was transferred to an anaerobic operation box, after which 0.2 g of the feces sample was suspended in 1 mL of sterile PBS solution and mixed thoroughly, in which the anaerobic gas components in the anaerobic operation box are $N_2:CO_2:H_2$=90:5:5. The suspension solution was diluted in gradient, 100 µL of the diluted solution was spread onto culture plates containing culture medium, and cultured under anaerobic conditions at 37° C. for 3-4 days. After culture for 3-4 days, a single colony was picked out and streaked in culture medium for strain isolation, thus obtaining a pure culture of single strain, followed by identification and functional verification.

1.1.6.3 16S rDNA Identification of Strain

The isolated pure culture strains were subjected to 16S rDNA sequencing to obtain classification information of each strain. The isolated single strain was further cultured in PYG liquid medium for 24 hours. 1 mL of the bacterial liquid was centrifuged at 10000 r/min for 5 minutes, and bacterial cells were collected for extraction of genomic DNA of the isolated strain. The PCR amplification for 16S rDNA sequence was performed by using the genomic DNA as a template and 16S rDNA universal primers. The 16S rDNA amplified product was subjected to purification and sequencing in a 3730 sequencer to obtain the 16S rDNA sequence of corresponding strain. After that, the 16S rDNA sequence obtained was aligned to the NCBI database for identification of strain.

The 16S rDNA universal primers and the PCR amplification system for 16S rDNA sequence are the same as those recited in "1.1.1.2 16S rDNA identification of strain". The amplification condition for 16S rDNA sequence are the same as those recited in "1.1.2.2 16S rDNA identification of strain".

The sequenced results showed that the 16S rDNA sequence of the isolated strain TF08-1 is of the sequence of SEQ ID NO. 6. The alignment results via NCBI Blast showed that the TF08-1 strain isolated in this example has the highest homology with *Lactobacillus gasseri*, with a similarity of 99.9%. Thus, the TF08-1 strain was determined to belong to *Lactobacillus gasseri* species, named as *Lactobacillus gasseri* TF08-1 and deposited.

1.1.7 *Lactobacillus acidophilus* AM13-1

The *Lactobacillus acidophilus* AM13-1 in this example was cultured using PYG medium under anaerobic conditions at 37° C. The colonies of the AM13-1 strain after cultured in the PYG medium for 2 days are white, convex, viscous, opaque, round, with neat edges, and has a diameter of about 2-3 mm. The microscopic morphology of the bacterium is rod-shaped, gram-positive, and does not produce spores and flagella. The *Lactobacillus acidophilus* AM13-1 is deposited in the Guangdong Microbial Culture Collection Center, with a deposit number of GDMCC 60091.

The specific steps of isolation and identification of *Lactobacillus acidophilus* AM13-1 are as follows.

1.1.7.1 Separation and Cultivation of Strain

The *Lactobacillus acidophilus* AM13-1 in this experiment was isolated from a feces sample of a healthy male in Shenzhen. The steps for strain isolation are as follows.

(1) The collected sample was transferred to an anaerobic operation box, after which 0.2 g of the sample was suspended in 1 mL of PBS solution, thoroughly mixed and diluted in gradient.

(2) 100 μL of the diluted solution was spread onto culture plates containing PYG medium and cultured under anaerobic conditions at 37° C., in which the anaerobic gas components in the anaerobic operation box are $N_2:H_2:CO_2=90:5:5$. The PYG medium is the same as that in "1.1.6.2 Separation and cultivation of strain".

(3) After culture for 4 days, a single colony generated in the culture plate was picked out and streaked in culture medium for strain isolation, followed by further culture under anaerobic conditions at 37° C.

(4) The pure culture of single strain obtained was stored for glycerol freeze preservation or for vacuum freeze-drying preservation.

1.1.7.2 16S rDNA Identification of Strain

The genomic DNA of individual isolated strain was extracted, followed by PCR amplification via using the genomic DNA as a template and 16S rDNA universal primers. The 16S rDNA amplified product was subjected to purification and sequencing in a 3730 sequencer to obtain the 16S rDNA sequence of corresponding strain. After that, the 16S rDNA sequence obtained was aligned to the NCBI database for identification of strain.

The 16S rDNA universal primers and the PCR amplification system for 16S rDNA sequence are the same as those recited in "1.1.1.2 16S rDNA identification of strain". The amplification condition for 16S rDNA sequence are the same as those recited in "1.1.2.2 16S rDNA identification of strain".

The sequenced results showed that the 16S rDNA sequence of the isolated strain AM13-1 is of the sequence of SEQ ID NO. 7. The alignment results via NCBI Blast showed that the AM13-1 strain isolated in this example has the highest homology with *Lactobacillus acidophilus*, with a similarity of 100%. Thus, the AM13-1 strain was determined to belong to *Lactobacillus acidophilus* species, named as *Lactobacillus acidophilus* AM13-1 and deposited.

1.2 Mouse Model

The mouse model selected in this example was an ulcerative colitis mouse model induced by dextran sodium sulfate (DSS, the molecular weight of 36000 to 50000).

Specifically, a C57bl/6 mouse strain purchased from Hubei Medical Experimental Animal Center was applied. 84 mice were all 8 weeks old, weighing 20 g±2 g, and were raised in an SPF-level mouse house environment. 84 mice were randomly divided into 7 groups, with 12 mice in each group for follow-up experiments.

DSS modeling: Each mouse was given with 0.15% of DSS for seven days to obtain the ulcerative colitis mouse model.

1.3 Test Method 84 mice were randomly divided into 7 groups, with 12 mice in each group. The 7 groups were normal group (i.e. a control group), a model group, a composition treatment group, a bacteria combination 1 treatment group, a bacteria combination 2 treatment group, a bacteria combination 3 treatment group, a bacteria combination 4 treatment group and a VSL#3 treatment group, respectively. The 7 groups were specifically treated as follows.

Normal group (i.e. a control group): each mouse was fed with common feed and given with 0.2 mL of PBS buffer per day.

Model group: each mouse was fed with the same common feed and subjected to DSS molding by adding DSS into drinking water of mice in a final concentration of 0.15% DSS and feeding mice with the DSS-included water for seven days, and given with 0.2 mL of PBS buffer per day.

Composition treatment group: each mouse was fed with the same common feed and intragastrically given with 0.2 ml of the composition bacterial solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the composition bacterial solution daily during the DSS modeling period.

Bacteria combination 1 treatment group: each mouse was fed with the same common feed and intragastrically given with 0.2 ml of the bacteria combination 1 solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the bacteria combination 1 solution daily during the DSS modeling period.

Bacteria combination 2 treatment group: each mouse was fed with the same common feed and intragastrically given with 0.2 ml of the bacteria combination 2 solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the bacteria combination 2 solution daily during the DSS modeling period.

Bacteria combination 3 treatment group: each mouse was fed with the same common feed and intragastrically given with 0.2 ml of the bacteria combination 3 solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the bacteria combination 3 solution daily during the DSS modeling period.

Bacteria combination 4 treatment group: each mouse was fed with the same common feed and intragastrically given with 0.2 ml of the bacteria combination 4 solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the bacteria combination 4 solution daily during the DSS modeling period.

VSL#3 treatment group: each mouse was fed with the same common feed and intragastrically given with 0.2 ml of the VSL#3 solution daily 3 days before DSS modeling. The DSS modeling was performed by adding DSS into drinking water of mice in a final concentration of 0.15% DSS and feeding mice with the DSS-included water for seven days, and intragastrically giving 0.2 mL of the VSL#3 solution daily during the DSS modeling period.

Among them, the composition bacterial solution, the bacteria combination 1 solution, the bacteria combination 2 solution, the bacteria combination 3 solution and the bacteria combination 4 solution were respectively formulated by the following steps.

*Megamonas funiformis* AF24-28AC, *Anaerofustis stercorihominis* AM25-6, *Collinsella shenzhenensis* TF06-26, *Roseburia inulinivorans* DSM 16841, *Butyribacter intestini* TF01-11, *Lactobacillus gasseri* TF08-1, and *Lactobacillus acidophilus* AM13-1 were respectively cultured for 24 hours, bacteria cells were collected by centrifugation followed by suspended with PBS buffer and adjusted to a concentration of $10^9$ cfu/mL, for further formulation of bacterial suspension.

Composition bacterial solution: the bacterial suspension of *Megamonas funiformis* AF24-28AC and the bacterial suspension of *Anaerofustis stercorihominis* AM25-6 were mixed in equal volume to obtain the composition bacterial solution.

Bacteria combination 1 solution: the bacterial suspension of *Megamonas funiformis* AF24-28AC, the bacterial suspension of *Anaerofustis stercorihominis* AM25-6 and the bacterial suspension of *Collinsella shenzhenensis* TF06-26 were mixed in equal volume to obtain the bacteria combination 1 solution.

Bacteria combination 2 solution: the bacterial suspension of *Megamonas funiformis* AF24-28AC, the bacterial suspension of *Anaerofustis stercorihominis* AM25-6 and the bacterial suspension of *Roseburia inulinivorans* DSM 16841 were mixed in equal volume to obtain the bacteria combination 2 solution.

Bacteria combination 3 solution: the bacterial suspension of *Megamonas funiformis* AF24-28AC, the bacterial suspension of *Anaerofustis stercorihominis* AM25-6 and the bacterial suspension of *Butyribacter intestini* TF01-11 were mixed in equal volume to obtain the bacteria combination 3 solution.

Bacteria combination 4 solution: the bacterial suspension of *Megamonas funiformis* AF24-28AC, the bacterial suspension of *Anaerofustis stercorihominis* AM25-6, the bacterial suspension of *Lactobacillus gasseri* TF08-1, and the bacterial suspension of *Lactobacillus acidophilus* AM13-1 were mixed in equal volume to obtain the bacteria combination 4 solution.

VSL#3 bacterial solution was formulated by the following steps.

VSL#3 was purchased from ALFASIGMA, USA, which is a probiotics compound containing 8 kinds of beneficial bacteria, including *Lactobacillus casei, Lactobacillus plantarum, Lactobacillus acidophilus, Lactobacillus delbrueckii* subsp. *bulgaricus, Streptococcus thermophilu, Bifidobacterium longum, Bifidobacterium breve* and *Bifidobacterium infantis*. The VSL#3 was suspended with the PBS buffer and adjusted to a concentration of $10^9$ cfu/mL, thus obtaining the VSL#3 bacterial solution.

After the DSS model was established, the weight, diet and drinking of the mice were recorded every day, and the fecal characteristics and occult blood of the mice were observed at the same time. The disease activity index (abbreviated as DAI) of the mice was calculated on day 1, day 3, day 5 and day 7, and DAI scoring standards are detailed in Table 2. After the completion of the experiment, the mice were all sacrificed, followed by taking blood, necked off, taking colon, taking photoes and measuring weight and the length of colon. The colon tissue was stored in a refrigerator at −80° C. and in paraformaldehyde. The normal group was recorded for a time the same as that for construction of the DSS model.

TABLE 2

DAI Index Scoring Table

| Weight loss (%) | fecal characteristics | fecal occult blood/ visible bleeding | Score |
| --- | --- | --- | --- |
| 0 | normal feces | normal feces | 0 |
| 1-5 | | | 1 |
| 5-10 | loose stool | presence of blood | 2 |
| 10-15 | | | 3 |
| >15 | watery diarrhea | visible bleeding | 4 |

For the "fecal characteristics" in Table 2, the "normal feces" means that the feces is shaped, the "loose stool" means that the feces is viscous and semi-shaped but not adheres to anus, and the "watery diarrhea" means that the feces is watery and can adhere to anus. For the "fecal occult blood/visible bleeding" in table 2, the "normal feces" means that occult blood is negative, the "visible bleeding" means the feces has red or brown blood, and the "presence of blood" means that the blood is not naked-eye visible but can be detected with tetramethyl benzidine. The DAI index refers to the sum of integral of "weight loss", "fecal characteristics" and "fecal occult blood/visible bleeding".

1.4 Results and Analysis
1.4.1 Weight Changes

The mice were weighed on day 1, day 3, day 5 and day 7, respectively. The average weight of the mice in each group is shown in Table 3 and FIG. 1.

TABLE 3

Average weight of mice

| Groups | Day 1 (g) | Day 3 (g) | Day 5 (g) | Day 7 (g) |
| --- | --- | --- | --- | --- |
| Control | 22.32 ± 0.45 | 23.73 ± 0.64 | 24.98 ± 0.96 | 25.52 ± 1.26 |
| Model | 22.41 ± 0.52 | 21.65 ± 0.71* | 20.02 ± 1.26* | 18.21 ± 1.57** |
| composition | 22.09 ± 0.47 | 21.59 ± 0.81 | 21.42 ± 1.37▲ | 20.81 ± 1.75▲ |
| bacteria combination 1 | 22.37 ± 0.51 | 21.71 ± 0.79 | 21.39 ± 1.40▲ | 20.79 ± 1.68▲ |
| bacteria combination 2 | 22.28 ± 0.60 | 21.61 ± 0.87 | 21.35 ± 1.54▲ | 20.72 ± 1.86▲ |
| bacteria combination 3 | 22.14 ± 0.52 | 21.69 ± 0.74 | 21.40 ± 1.49▲ | 20.78 ± 1.84▲ |
| bacteria combination 4 | 22.48 ± 0.57 | 22.03 ± 0.86 | 21.74 ± 1.28 | 20.82 ± 1.49▲ |
| VSL#3 | 22.54 ± 0.71 | 21.87 ± 0.92 | 21.32 ± 1.48 | 20.01 ± 1.66▲ |

In Table 3, "control" refers to the normal group, "composition" refers to the composition treatment group, "bacteria combination 1" refers to the bacteria combination 1 treatment group, "bacteria combination 2" refers to the bacteria combination 2 treatment group, "bacteria combination 3" refers to the bacteria combination 3 treatment groups, "bacteria combination 4" refers to the bacteria combination 4 treatment group and "VSL#3" refers to the VSL#3 treatment group. "*" refers to that the significant level of weight difference between mice of the model group and the normal group is $P<0.05$, "**" refers to that the significant level of weight difference between mice of the model group and the normal group is $P<0.01$, and "▲" refers to that the significant level of weight difference between mice of the model group and the "composition" group, the "bacteria combination 1" group, the "bacteria combination 2" group, the "bacteria combination 3" group, the "bacteria combination 4" group or the "VSL#3" group is $P<0.05$.

The results in Table 3 and FIG. 1 show that the weight of mice in the control group is slowly increased, whereas the weight of mice in the seven DSS-induced groups continues to decrease. On day 3, the weight of mice in the model group began to decrease significantly compared to the control group (*$P<0.05$). On day 7, the weight difference between the model group and the control group was more significant (**$P<0.01$). The intervention of the composition, the bacteria combination 1, the bacteria combination 2, the bacteria combination 3, the bacteria combination 4 or the VSL#3 can slow down the weight loss of UC mice. On day 7, the weight loss of mice in the composition, the bacteria combination 1, the bacteria combination 2, the bacteria combination 3, the bacteria combination 4 and the VSL#3 groups was controlled significantly compared to the model group (▲$P<0.05$). The results show that the composition including *Megamonas funiformis* AF24-28AC and *Anaerofustis stercorihominis* AM25-6, as well as the bacteria combinations 1-4, and the VSL#3 can all control the weight loss caused by UC disease. On day 7, the weight of mice in the composition group (including *Megamonas funiformis* AF24-28AC and *Anaerofustis stercorihominis* AM25-6) as well as the bacteria combinations 1-4 groups, was slightly higher than the VSL#3 group, indicating that the composition (including *Megamonas funiformis* AF24-28AC and *Anaerofustis stercorihominis* AM25-6), as well as the bacteria combinations (including *Megamonas funiformis* AF24-28AC and *Anaerofustis stercorihominis* AM25-6 in combination of other probiotics) can achieve a better effect than VSL#3 on controlling weight loss of UC mice.

1.4.2 DAI Changes

DAI index of DSS-induced UC mice was changed due to the changes in weight loss, fecal characteristics and fecal occult blood. The statistical values of DAI index of mice on day 1, day 3, day 5 and day 7 are shown in Table 4 and FIG. 2. In Table 4, the DAI index of mice in each group is averaged.

TABLE 4

DAI value of mice

| Groups | Day 1 | Day 3 | Day 5 | Day 7 |
| --- | --- | --- | --- | --- |
| Control | 1.1 ± 0.5 | 1.1 ± 0.7 | 1.2 ± 0.8 | 1.3 ± 0.8 |
| Model | 1.1 ± 0.5 | 3.6 ± 1.1* | 7.2 ± 1.6** | 9.4 ± 2.0** |
| composition | 1.1 ± 0.4 | 3.4 ± 1.2 | 6.0 ± 1.7▲ | 6.8 ± 2.1▲ |
| bacteria combination 1 | 1.2 ± 0.7 | 3.3 ± 1.4 | 5.9 ± 1.8▲ | 6.7 ± 2.0▲ |
| bacteria combination 2 | 1.1 ± 0.6 | 3.2 ± 1.3 | 5.8 ± 1.6▲ | 6.8 ± 2.0▲ |
| bacteria combination 3 | 1.1 ± 0.7 | 3.2 ± 1.5 | 6.0 ± 1.7▲ | 6.9 ± 1.9▲ |
| bacteria combination 4 | 1.1 ± 0.4 | 3.3 ± 0.9 | 5.5 ± 1.4▲ | 6.7 ± 1.7▲ |
| VSL#3 | 1.1 ± 0.4 | 3.4 ± 1.3 | 6.6 ± 1.6 | 7.8 ± 1.9▲ |

In Table 4, "control" refers to the normal group, "composition" refers to the composition treatment group, "bacteria combination 1" refers to the bacteria combination 1 treatment group, "bacteria combination 2" refers to the bacteria combination 2 treatment group, "bacteria combination 3" refers to the bacteria combination 3 treatment groups, "bacteria combination 4" refers to the bacteria combination 4 treatment group and "VSL#3" refers to the VSL#3 treatment group. "*" refers to that the significant level of DAI index difference between mice of the model group and the normal group is $P<0.05$, "**" refers to that the significant level of DAI index difference between mice of the model group and the normal group is $P<0.01$, and "▲" refers to that the significant level of DAI index difference between mice of the model group and the "composition", the "bacteria combination 1", the "bacteria combination 2", the "bacteria combination 3", the "bacteria combination 4" or the "VSL#3" is P<0.05.

Figure 2:
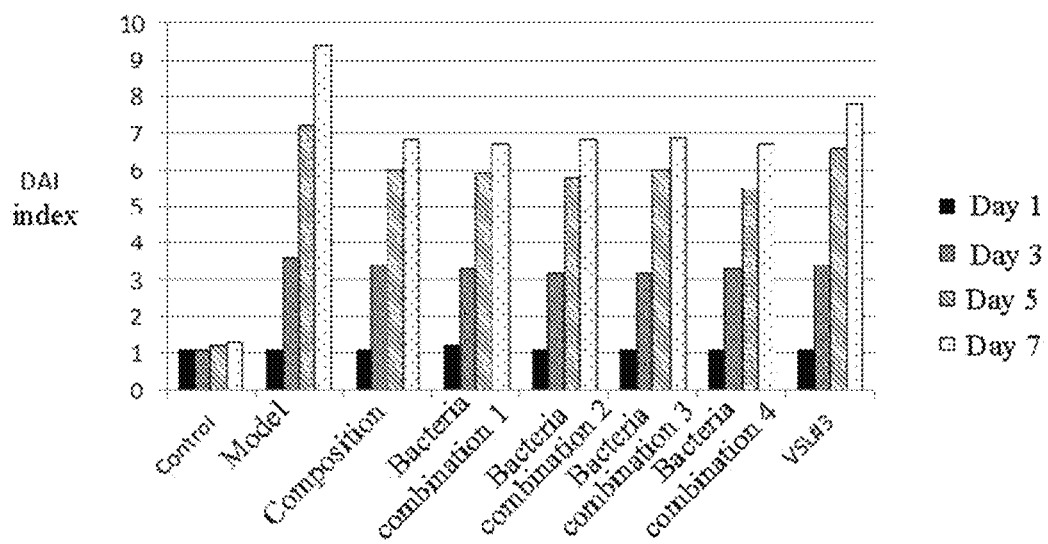
FIG. 2 is a graph showing the change of DAI index of mice in a control group, a model group, a VSL[#]3 group, a composition treatment group, a bacteria combination 1 treatment group, a bacteria combination 2 treatment group, a bacteria combination 3 treatment group or a bacteria combination 4 treatment group in examples of this application.

The data in Table 4 and FIG. 2 show that the DAI of mice in the control group is basically unchanged, whereas the DAI of mice in the model group, the composition group, the bacteria combinations 1-4 groups and the VSL#3 group is gradually increased with the induction of DSS. On day 3, the DAI of mice in the model group began to increase significantly compared to the control group (*P<0.05). On day 7, the DAI of mice in the model group reached the highest level compared to the control group (**P<0.01). The intervention of the composition (including *Megamonas funiformis* AF24-28AC and *Anaerofustis stercorihominis* AM25-6), as well as the bacteria combinations 1-4 (including *Megamonas funiformis* AF24-28AC and *Anaerofustis stercorihominis* AM25-6 in combination of other probiotics) can control the increase of DAI, in which the DAI of mice in the composition group and the bacteria combinations 1-4 groups is significantly controlled on day 5 and day 7 compared to the model group (▲P<0.05). Further, the DAI of mice in the composition group and the bacteria combinations 1-4 groups is slightly lower than the VSL#3 group on day 7, which indicates that the composition (including *Megamonas funiformis* AF24-28AC and *Anaerofustis stercorihominis* AM25-6) and the bacteria combinations 1-4 (including *Megamonas funiformis* AF24-28AC and *Anaerofustis stercorihominis* AM25-6 in combination of other probiotics) can have a better effect than VSL#3 on controlling DAI increase of UC mice.

1.4.3 Changes of Colon Length

The colon tissue of UC model mice can be changed because the ulcers and inflammation cause the shortening of colon tissue. After the treatment, the colon length of mice measured by anatomy is shown in Table 5.

TABLE 5 colon length of mice

| Groups | colon length (cm) |
|---|---|
| Control | 8.38 ± 0.49 |
| Model | 5.02 ± 0.87** |
| VSL#3 | 6.10 ± 0.67▲ |
| composition | 6.53 ± 0.62▲ |
| bacteria combination 1 | 6.61 ± 0.78▲ |
| bacteria combination 2 | 6.58 ± 0.79▲ |
| bacteria combination 3 | 6.69 ± 0.81▲ |
| bacteria combination 4 | 6.62 ± 0.79▲ |

In Table 5, "control" refers to the normal group, "composition" refers to the composition treatment group, "bacteria combination 1" refers to the bacteria combination 1 treatment group, "bacteria combination 2" refers to the bacteria combination 2 treatment group, "bacteria combination 3" refers to the bacteria combination 3 treatment groups, "bacteria combination 4" refers to the bacteria combination 4 treatment group and "VSL#3" refers to the VSL#3 treatment group. "**" refers to that the significant level of colon length difference between mice of the model group and the normal group is P<0.01, and "▲" refers to that the significant level of colon length difference between mice of the model group and the "composition", the "bacteria combination 1", the "bacteria combination 2", the "bacteria combination 3", the "bacteria combination 4" or the "VSL#3" is P<0.05.

The results in Table 5 show that the colon tissue of mice in the model group is shortened significantly 7 days after DSS induction, which is also greatly significant compared to the control group (**P<0.01). The intervention of the composition, the bacteria combination 1, the bacteria combination 2, the bacteria combination 3, the bacteria combination 4 or the VSL#3 can significantly control the colon shortening of mice, which is very significant compared to the model group (*P<0.05). According to the data in Table 5, it can be found that the colon length of mice intervened by the composition or bacteria combinations 1-4 is longer than that of mice in the VSL#3 group, indicating that the composition (including *Megamonas funiformis* AF24-28AC and *Anaerofustis stercorihominis* AM25-6), as well as the bacteria combinations (including *Megamonas funiformis* AF24-28AC and *Anaerofustis stercorihominis* AM25-6 in combination of other probiotics) can has a stronger ability than VSL#3 on controlling the colon shortening of UC mice.

The results of Tables 3 to 5 and FIGS. 1 and 2 show that the composition and the bacteria combinations 1-4 thereof in the example have efficacy on preventing or treating ulcerative colitis, and the treatment effect achieved is slightly better than that of the VSL#3 product.

Example 2

In this example, the composition including *Megamonas funiformis* AF24-28AC and *Anaerofustis stercorihominis* AM25-6, which was proven to be effective in treatment or prevention of ulcerative colitis, was made into a food composition.

In specific, those cultured *Megamonas funiformis* AF24-28AC and *Anaerofustis stercorihominis* AM25-6 were formulated together with excipients (such as milk, vitamin C and sugar) in accordance with Table 6, thereby preparing a food composition useful in treatment or prevention of ulcerative colitis.

TABLE 6

Formulation of the food composition

| ingredient | mass percentage (%) |
|---|---|
| *Megamonas funiformis* AF24-28AC | 0.3 |
| *Anaerofustis stercorihominis* AM25-6 | 0.3 |
| milk | 90.0 |
| sugar | 8.8 |
| Vitamin C | 0.6 |

In accordance with the formulated ratios shown in Table 6, milk and sugar were mixed thoroughly before subjected to preheating, homogenizing under a pressure of 20 Mpa, sterilizing around 90° C. for 5 to 10 min, and cooling to 40 to 43° C. Afterwards, a protective agent (i.e., vitamin C) was added and then *Megamonas funiformis* AF24-28AC and *Anaerofustis stercorihominis* AM25-6 were inoculated at $1-100 \times 10^6$ cfu/g, thereby giving a food composition containing such two bacterial strains.

The food composition prepared in the present Example was added into the DSS-modeling feedstuff for mice in the composition treatment group. The feeding scheme and detecting scheme are same as Example 1, except that the mice in the composition treatment group were fed with the modeling feedstuff together with the food composition prepared in the present example, instead of being administered with the bacterial suspension containing the composition by gavage. The detection results show that the food composition prepared in the present Example is also capable of controlling weight loss of the UC mice, reducing disease activity index (DAI) of mice and ameliorating the intestinal lesion (i.e., bowel lesion), thus being useful in treatment or prevention of ulcerative colitis.

Example 3

In this example, the composition of the bacteria combination 1, proven to be effective in treatment or prevention of ulcerative colitis, was made into a food composition.

In specific, those cultured *Megamonas funiformis* AF24-28AC, *Anaerofustis stercorihominis* AM25-6, and *Collinsella shenzhenensis* TF06-26 were formulated together with excipients (such as milk, vitamin C and sugar) in accordance with Table 7, thereby preparing a food composition and being useful in treatment or prevention of ulcerative colitis.

TABLE 7

Formulation of the food composition

| ingredient | mass percentage (%) |
|---|---|
| *Megamonas funiformis* AF24-28AC | 0.2 |
| *Anaerofustis stercorihominis* AM25-6 | 0.2 |
| *Collinsella shenzhenensis* TF06-26 | 0.2 |
| milk | 90.0 |
| sugar | 8.8 |
| Vitamin C | 0.6 |

In accordance with the formulated ratios shown in Table 7, milk and sugar were mixed thoroughly before subjected to preheating, homogenizing under a pressure of 20 Mpa, sterilizing around 90° C. for 5 to 10 min, and cooling to 40 to 43° C. Afterwards, a protective agent (i.e., vitamin C) was added and then *Megamonas funiformis* AF24-28AC, *Anaerofustis stercorihominis* AM25-6, and *Collinsella shenzhenensis* TF06-26 were inoculated at 1-100×10$^6$ cfu/g, thereby giving a food composition containing such three bacteria strains.

The food composition prepared in the present Example was added into the DSS-modeling feedstuff for mice in the bacteria combination 1 treatment group. The feeding scheme and detecting scheme are same as Example 1, except that the mice in the bacteria combination 1 treatment group were fed with the modeling feedstuff together with the food composition prepared in the present example, instead of being administered with the bacterial suspension containing the bacteria combination 1 by gavage. The detection results show that the food composition prepared in the present Example is also capable of controlling weight loss of the UC mice, reducing disease activity index (DAI) of mice and ameliorating the intestinal lesion, thus being useful in treatment or prevention of ulcerative colitis.

Example 4

In this example, the composition of the bacteria combination 2, proven to be effective in treatment or prevention of ulcerative colitis, was made into a food composition.

In specific, those cultured *Megamonas funiformis* AF24-28AC, *Anaerofustis stercorihominis* AM25-6, and *Roseburia inulinivorans* DSM 16841 were formulated together with excipients (such as milk, vitamin C and sugar) in accordance with Table 8, thereby preparing a food composition and being useful in treatment or prevention of ulcerative colitis.

TABLE 8

Formulation of the food composition

| ingredient | mass percentage (%) |
|---|---|
| *Megamonas funiformis* AF24-28AC | 0.2 |
| *Anaerofustis stercorihominis* AM25-6 | 0.2 |
| *Roseburia inulinivorans* DSM 16841 | 0.2 |
| milk | 90.0 |
| sugar | 8.8 |
| Vitamin C | 0.6 |

In accordance with the formulated ratios shown in Table 8, milk and sugar were mixed thoroughly before subjected to preheating, homogenizing under a pressure of 20 Mpa, sterilizing around 90° C. for 5 to 10 min, and cooling to 40 to 43° C. Afterwards, a protective agent (i.e., vitamin C) was added and then *Megamonas funiformis* AF24-28AC, *Anaerofustis stercorihominis* AM25-6, and *Roseburia inulinivorans* DSM 16841 were inoculated at 1-100×10$^6$ cfu/g, thereby giving a food composition containing such three bacteria strains.

The food composition prepared in the present Example was added into the DSS-modeling feedstuff for mice in the bacteria combination 2 treatment group. The feeding scheme and detecting scheme are same as Example 1, except that the mice in the bacteria combination 2 treatment group were fed with the modeling feedstuff together with the food composition prepared in the present example, instead of being administered with the bacterial suspension containing the bacteria combination 2 by gavage. The detection results show that the food composition prepared in the present Example is also capable of controlling weight loss of the UC mice, reducing disease activity index (DAI) of mice and ameliorating the intestinal lesion, thus being useful in treatment or prevention of ulcerative colitis.

Example 5

In this example, the composition of the bacteria combination 3, proven to be effective in treatment or prevention of ulcerative colitis, was made into a food composition.

In specific, those cultured *Megamonas funiformis* AF24-28AC, *Anaerofustis stercorihominis* AM25-6, and *Butyribacter intestini* TF01-11 were formulated together with excipients (such as milk, vitamin C and sugar) in accordance with Table 9, thereby preparing a food composition and being useful in treatment or prevention of ulcerative colitis.

TABLE 9

Formulation of the food composition

| ingredient | mass percentage (%) |
|---|---|
| *Megamonas funiformis* AF24-28AC | 0.2 |
| *Anaerofustis stercorihominis* AM25-6 | 0.2 |
| *Butyribacter intestini* TF01-11 | 0.2 |
| milk | 90.0 |
| sugar | 8.8 |
| Vitamin C | 0.6 |

In accordance with the formulated ratios shown in Table 9, milk and sugar were mixed thoroughly before subjected to preheating, homogenizing under a pressure of 20 Mpa, sterilizing around 90° C. for 5 to 10 min, and cooling to 40 to 43° C. Afterwards, a protective agent (i.e., vitamin C) was added and then *Megamonas funiformis* AF24-28AC, *Anaerofustis stercorihominis* AM25-6, and *Butyribacter* intestini TF01-11 were inoculated at 1-100×10⁶ cfu/g, thereby giving a food composition containing such three bacteria strains.

The food composition prepared in the present Example was added into the DSS-modeling feedstuff for mice in the bacteria combination 3 treatment group. The feeding scheme and detecting scheme are same as Example 1, except that the mice in the bacteria combination 3 treatment group were fed with the modeling feedstuff together with the food composition prepared in the present example, instead of being administered with the bacterial suspension containing the bacteria combination 3 by gavage. The detection results show that the food composition prepared in the present Example is also capable of controlling weight loss of the UC mice, reducing disease activity index (DAI) of mice and ameliorating the intestinal lesion, thus being useful in treatment or prevention of ulcerative colitis.

Example 6

In this example, the composition of the bacteria combination 4, proven to be effective in treatment or prevention of ulcerative colitis, was made into a food composition.

In specific, those cultured *Megamonas funiformis* AF24-28AC, *Anaerofustis stercorihominis* AM25-6, *Lactobacillus gasseri* TF08-1, and *Lactobacillus acidophilus* AM13-1 were formulated together with excipients (such as milk, vitamin C and sugar) in accordance with Table 10, thereby preparing a food composition and being useful in treatment or prevention of ulcerative colitis.

TABLE 10

Formulation of the food composition

| ingredient | mass percentage (%) |
| --- | --- |
| *Megamonas funiformis* AF24-28AC | 0.15 |
| *Anaerofustis stercorihominis* AM25-6 | 0.15 |
| *Lactobacillus gasseri* TF08-1 | 0.15 |
| *Lactobacillus acidophilus* AM13-1 | 0.15 |
| milk | 90.0 |
| sugar | 8.8 |
| Vitamin C | 0.6 |

In accordance with the formulated ratios shown in Table 10, milk and sugar were mixed thoroughly before subjected to preheating, homogenizing under a pressure of 20 Mpa, sterilizing around 90° C. for 5 to 10 min, and cooling to 40 to 43° C. Afterwards, a protective agent (i.e., vitamin C) was added and then *Megamonas funiformis* AF24-28AC, *Anaerofustis stercorihominis* AM25-6, *Lactobacillus gasseri* TF08-1, and *Lactobacillus acidophilus* AM13-1 were inoculated at 1-100×10⁶ cfu/g, thereby giving a food composition containing such four bacteria strains.

The food composition prepared in the present Example was added into the DSS-modeling feedstuff for mice in the bacteria combination 4 treatment group. The feeding scheme and detecting scheme are same as Example 1, except that the mice in the bacteria combination 4 treatment group were fed with the modeling feedstuff together with the food composition prepared in the present example, instead of administered with the bacterial suspension containing the bacteria combination 4 by gavage. The detection results show that the food composition prepared in the present Example is also capable of controlling weight loss of the UC mice, reducing disease activity index (DAI) of mice and ameliorating the intestinal lesion, thus being useful in treatment or prevention of ulcerative colitis.

Example 7

In this example, the composition including *Megamonas funiformis* AF24-28AC and *Anaerofustis stercorihominis* AM25-6, which was proven to be effective in treatment or prevention of ulcerative colitis, was made into a medicament composition for treating ulcerative colitis, in accordance with the formulation in Table 11.

TABLE 11

Formulation of the medicament composition

| ingredient | mass percentage (%) |
| --- | --- |
| *Megamonas funiformis* AF24-28AC | 0.75% |
| *Anaerofustis stercorihominis* AM25-6 | 0.75% |
| lactose | 2.0% |
| yeast powders | 2.0% |
| peptone | 1.0% |
| purified water | 93% |
| Vitamin C | 0.5% |

In accordance with the formulated ratios shown in Table 11, lactose, yeast powders, and peptone were mixed thoroughly in purified water, before subjected to preheating to 60 to 65° C., homogenizing under a pressure of 20 Mpa, sterilizing around 90° C. for 20 to 30 min, and cooling to 36 to 38° C. Afterwards, a protective agent (i.e., vitamin C) was added and then active bacteria strains (*Megamonas funiformis* AF24-28AC and *Anaerofustis stercorihominis* AM25-6) were inoculated at 1-50×10⁶ cfu/g individually, followed by fermentation at 36 to 38° C. until achieving a pH value of 6.0, centrifuge and lyophilization till a water content below 3%, thereby giving a freeze-dried product. 0.5 g of the freeze-dried product was mixed with maltodextrin at the equivalent ratio, and capsulated into a capsule, thus obtaining a medicament composition, in the form of capsules, containing *Megamonas funiformis* AF24-28AC and *Anaerofustis stercorihominis* AM25-6.

The medicament composition in the form of capsules prepared in the present Example was replaced for the bacterial suspension of the composition in Example 1. To the mice in the composition treatment group, the medicament composition in the form of capsules prepared in the present Example was administered by gavage, one capsule per day, in accordance with the treating scheme and detecting scheme same as Example 1. The results show that the medicament composition in the form of capsules prepared in the present Example is also capable of controlling weight loss of the UC mice, reducing disease activity index (DAI) of mice and ameliorating the intestinal lesion, thus being useful in treatment or prevention of ulcerative colitis.

Example 8

In this example, the composition of the bacteria combination 1, proven to be effective in treatment or prevention of ulcerative colitis, was made into a medicament composition for treating ulcerative colitis, in accordance with the formulation in Table 12.

TABLE 12

| Formulation of the medicament composition | |
|---|---|
| ingredient | mass percentage (%) |
| Megamonas funiformis AF24-28AC | 0.75% |
| Anaerofustis stercorihominis AM25-6 | 0.75% |
| Collinsella shenzhenensis TF06-26 | 0.75% |
| lactose | 2.0% |
| yeast powders | 2.0% |
| peptone | 1.0% |
| purified water | 92.25% |
| Vitamin C | 0.5% |

In accordance with the formulated ratios shown in Table 12, lactose, yeast powders, and peptone were mixed thoroughly in purified water, before subjected to preheating to 60 to 65° C., homogenizing under a pressure of 20 Mpa, sterilizing around 90° C. for 20 to 30 min, and cooling to 36 to 38° C. Afterwards, a protective agent (i.e., vitamin C) was added and then active bacteria strains (Megamonas funiformis AF24-28AC, Anaerofustis stercorihominis AM25-6, and Collinsella shenzhenensis TF06-26) were inoculated at 1-50×10$^6$ cfu/g individually, followed by fermentation at 36 to 38° C. until achieving a pH value of 6.0, centrifuge and lyophilization till a water content below 3%, thereby giving a freeze-dried bacteria combination 1. 0.5 g of the freeze-dried bacteria combination 1 was mixed with maltodextrin at the equivalent ratio, and capsulated into a capsule, thus obtaining a medicament composition, in the form of capsules, containing Megamonas funiformis AF24-28AC, Anaerofustis stercorihominis AM25-6 and Collinsella shenzhenensis TF06-26.

The medicament composition in the form of capsules prepared in the present Example was replaced for the bacterial suspension of the bacteria combination 1 in Example 1. To the mice in the bacteria combination 1 treatment group, the medicament composition in the form of capsules prepared in the present Example was administered by gavage, one capsule per day, in accordance with the treating scheme and detecting scheme same as Example 1. The results show that the medicament composition in the form of capsules prepared in the present Example is also capable of controlling weight loss of the UC mice, reducing disease activity index (DAI) of mice and ameliorating the intestinal lesion, thus being useful in treatment or prevention of ulcerative colitis.

Example 9

In this example, the composition of the bacteria combination 2, proven to be effective in treatment or prevention of ulcerative colitis, was made into a medicament composition for treating ulcerative colitis, in accordance with the formulation in Table 13.

TABLE 13

| Formulation of the medicament composition | |
|---|---|
| ingredient | mass percentage (%) |
| Megamonas funiformis AF24-28AC | 0.75% |
| Anaerofustis stercorihominis AM25-6 | 0.75% |
| Roseburia inulinivorans DSM 16841 | 0.75% |
| lactose | 2.0% |
| yeast powders | 2.0% |
| peptone | 1.0% |
| purified water | 92.25% |
| Viitamin C | 0.5% |

In accordance with the formulated ratios shown in Table 13, lactose, yeast powders, and peptone were mixed thoroughly in purified water, before subjected to preheating to 60 to 65° C., homogenizing under a pressure of 20 Mpa, sterilizing around 90° C. for 20 to 30 min, and cooling to 36 to 38° C. Afterwards, a protective agent (i.e., vitamin C) was added and then active bacteria strains (Megamonas funiformis AF24-28AC, Anaerofustis stercorihominis AM25-6, and Roseburia inulinivorans DSM 16841) were inoculated at 1-50×10$^6$ cfu/g individually, followed by fermentation at 36 to 38° C. until achieving a pH value of 6.0, centrifuge and lyophilization till a water content below 3%, thereby giving a freeze-dried bacteria combination 2. 0.5 g of the freeze-dried bacteria combination 2 was mixed with maltodextrin at the equivalent ratio, and capsulated into a capsule, thus obtaining a medicament composition, in the form of capsules, containing Megamonas funiformis AF24-28AC, Anaerofustis stercorihominis AM25-6 and Roseburia inulinivorans DSM 16841.

The medicament composition in the form of capsules prepared in the present Example was replaced for the bacterial suspension of the bacteria combination 2 in Example 1. To the mice in the bacteria combination 2 treatment group, the medicament composition in the form of capsules prepared in the present Example was administered by gavage, one capsule per day, in accordance with the treating scheme and detecting scheme same as Example 1. The results show that the medicament composition in the form of capsules prepared in the present Example is also capable of controlling weight loss of the UC mice, reducing disease activity index (DAI) of mice and ameliorating the intestinal lesion, thus being useful in treatment or prevention of ulcerative colitis.

Example 10

In this example, the composition of the bacteria combination 3, proven to be effective in treatment or prevention of ulcerative colitis, was made into a medicament composition for treating ulcerative colitis, in accordance with the formulation in Table 14.

TABLE 14

| Formulation of the medicament composition | |
|---|---|
| ingredient | mass percentage (%) |
| Megamonas funiformis AF24-28AC | 0.75% |
| Anaerofustis stercorihominis AM25-6 | 0.75% |
| Butyribacter intestini TF01-11 | 0.75% |
| lactose | 2.0% |
| yeast powders | 2.0% |
| peptone | 1.0% |
| purified water | 92.25% |
| Vitamin C | 0.5% |

In accordance with the formulated ratios shown in Table 14, lactose, yeast powders, and peptone were mixed thoroughly in purified water, before subjected to preheating to 60 to 65° C., homogenizing under a pressure of 20 Mpa, sterilizing around 90° C. for 20 to 30 min, and cooling to 36 to 38° C. Afterwards, a protective agent (i.e., vitamin C) was added and then active bacteria strains (*Megamonas funiformis* AF24-28AC, *Anaerofustis stercorihominis* AM25-6, and *Butyribacter intestini* TF01-11) were inoculated at 1-50×10$^6$ cfu/g individually, followed by fermentation at 36 to 38° C. until achieving a pH value of 6.0, centrifuge and lyophilization till a water content below 3%, thereby giving a freeze-dried bacteria combination 3. 0.5 g of the freeze-dried bacteria combination 3 was mixed with maltodextrin at the equivalent ratio, and capsulated into a capsule, thus obtaining a medicament composition, in the form of capsules, containing *Megamonas funiformis* AF24-28AC, *Anaerofustis stercorihominis* AM25-6 and *Butyribacter intestini* TF01-11.

The medicament composition in the form of capsules prepared in the present Example was replaced for the bacterial suspension of the bacteria combination 3 in Example 1. To the mice in the bacteria combination 3 treatment group, the medicament composition in the form of capsules prepared in the present Example was administered by gavage, one capsule per day, in accordance with the treating scheme and detecting scheme same as Example 1. The results show that the medicament composition in the form of capsules prepared in the present Example is also capable of controlling weight loss of the UC mice, reducing disease activity index (DAI) of mice and ameliorating the intestinal lesion, thus being useful in treatment or prevention of ulcerative colitis.

Example 11

In this example, the composition of the bacteria combination 4, proven to be effective in treatment or prevention of ulcerative colitis, was made into a medicament composition for treating ulcerative colitis, in accordance with the formulation in Table 15.

TABLE 15

Formulation of the medicament composition

| ingredient | mass percentage (%) |
| --- | --- |
| *Megamonas funiformis* AF24-28AC | 0.75% |
| *Anaerofustis stercorihominis* AM25-6 | 0.75% |
| *Lactobacillus gasseri* TF08-1 | 0.5% |
| *Lactobacillus acidophilus* AM13-1 | 0.5% |
| lactose | 2.0% |
| yeast powders | 2.0% |
| peptone | 1.0% |
| purified water | 92% |
| Vitamin C | 0.5% |

In accordance with the formulated ratios shown in Table 15, lactose, yeast powders, and peptone were mixed thoroughly in purified water, before subjected to preheating to 60 to 65° C., homogenizing under a pressure of 20 Mpa, sterilizing around 90° C. for 20 to 30 min, and cooling to 36 to 38° C. Afterwards, a protective agent (i.e., vitamin C) was added and then active bacteria strains (*Megamonas funiformis* AF24-28AC, *Anaerofustis stercorihominis* AM25-6, *Lactobacillus gasseri* TF08-1, and *Lactobacillus acidophilus* AM13-1) were inoculated at 1-50×10$^6$ cfu/g individually, followed by fermentation at 36 to 38° C. until achieving a pH value of 6.0, centrifuge and lyophilization till a water content below 3%, thereby giving a freeze-dried bacteria combination 4. 0.5 g of the freeze-dried bacteria combination 4 was mixed with maltodextrin at the equivalent ratio, and capsulated into a capsule, thus obtaining a medicament composition, in the form of capsules, containing *Megamonas funiformis* AF24-28AC, *Anaerofustis stercorihominis* AM25-6, *Lactobacillus gasseri* TF08-1, and *Lactobacillus acidophilus* AM13-1.

The medicament composition in the form of capsules prepared in the present Example was replaced for the bacterial suspension of the bacteria combination 4 in Example 1. To the mice in the bacteria combination 4 treatment group, the medicament composition in the form of capsules prepared in the present Example was administered by gavage, one capsule per day, in accordance with the treating scheme and detecting scheme same as Example 1. The results show that the medicament composition in the form of capsules prepared in the present Example is also capable of controlling weight loss of the UC mice, reducing disease activity index (DAI) of mice and ameliorating the intestinal lesion, thus being useful in treatment or prevention of ulcerative colitis.

The above examples demonstrate the combination of *Megamonas funiformis* and *Anaerofustis stercorihominis* can treat or prevent ulcerative colitis. Besides, in the presence of the combination of *Megamonas funiformis* and *Anaerofustis stercorihominis*, adding each of *Collinsella shenzhenensis, Roseburia inulinivorans*, and *Butyribacter intestine*, or adding *Lactobacillus gasseri* and *Lactobacillus acidophilus*, can also treat and prevent ulcerative colitis. The foresaid combined compositions can be made as various foods or medicaments for use. In addition, it would be appreciated that the foresaid combined compositions can be made as both various foods or medicaments, and various health products or food additives.

Further, studies show that the therapeutic effect by the combination of *Megamonas funiformis* and *Anaerofustis stercorihominis* depends largely on improvement of microecology, which is effective in treatment or prevention of not only ulcerative colitis but also other microecology-related diseases, such as common enteritis and gastritis. Therefore, the compositions provided in examples of the present disclosure can be used in treatment or prevention of inflammation or inflammation-related diseases, especially enteritis and gastritis.

The description of above examples is for the purpose of further illustrating the present disclosure in detail with reference to specific embodiments, and thus cannot be construed to limit the present disclosure anyway. It would be appreciated by those ordinary skilled in the art that several simple deductions or substitutions can be made in the embodiments without departing from the concept of the present disclosure and thus belong to the scope of the present disclosure.

What is claimed is:

1. A method for treating or preventing inflammation or inflammation-related diseases, comprising administering a composition comprising *Megamonas funiformis* having the 16s rDNA sequence of SEQ ID NO.:3 and *Anaerofustis stercorihominis* having the 16s rDNA sequence of SEQ ID NO.:4 to a subject in need thereof, the inflammation or inflammation-related diseases are ulcerative colitis, common enteritis or gastritis.

2. The method according to claim 1, wherein the composition exhibits any activities from the group consisting of: controlling weight loss in a mammal, reducing a disease activity index of a mammal, and relieving intestinal lesion of a mammal.

3. The method according to claim 1, wherein the *Megamonas funiformis* having the 16s rDNA sequence of SEQ ID NO.:3 is *Megamonas funiformis* AF24-28AC with a deposit number of GDMCC 60093, and the *Anaerofustis stercorihominis* having the 16s rDNA sequence of SEQ ID NO.:4 is *Anaerofustis stercorihominis* AM25-6 with a deposit number of GDMCC 60087.

4. The method according to claim 1, wherein the composition further comprises *Collinsella shenzhenensis*.

5. The method according to claim 1, wherein the composition further comprises *Butyribacter intestini*.

6. The method according to claim 1, wherein the composition further comprises one or both of probiotics and prebiotics.

7. The method according to claim 1, wherein the composition further comprises a substance capable of maintaining the viability of at least one of the bacteria, wherein, the substance capable of maintaining the viability of at least one of the bacteria is at least one selected from the group consisting of cysteine, glutathione, butylated hydroxyanisole, dibutyl methyl toluene, tocopherol, antioxidant of bamboo leaves, D-isoascorbic acid or a sodium salt thereof, sodium ascorbate, calcium ascorbate, phospholipid, Vitamin C and Vitamin E.

8. The method according to claim 1, wherein the composition further comprises a pharmaceutically or food acceptable carrier.

9. The method according to claim 1, wherein the composition is in a form of a food, a health product, a food additive or a medicament.

10. The method according to claim 9, wherein the medicament is in a form of tablets, granules, powders, an enteric-coated agent, solutions or suspensions.

11. The method according to claim 1, wherein the administration dosage of the composition is 0.2 mL per day, wherein the concentration of the *Megamonas funiformis* having the 16s rDNA sequence of SEQ ID NO.:3 and the *Anaerofustis stercorihominis* having the 16s rDNA sequence of SEQ ID NO.:4 in the composition is $10^9$ cfu/mL.

12. The method according to claim 1, wherein the composition further comprises at least one of *Roseburia inulinivorans, Lactobacillus gasseri* and *Lactobacillus acidophilus*.

13. The method according to claim 4, wherein the *Collinsella shenzhenensis* is *Collinsella shenzhenensis* TF06-26 with a deposit number of GDMCC 60090.

14. The method according to claim 5, wherein the *Butyribacter intestini* is *Butyribacter intestini* TF01-11 with a deposit number of CGMCC 10984.

15. The method according to claim 12, wherein the *Roseburia inulinivorans* is *Roseburia inulinivorans* DSM 16841 with a deposit number of DSM 16841.

16. The method according to claim 12, wherein the *Lactobacillus gasseri* is *Lactobacillus gasseri* TF08-1 with a deposit number of GDMCC 60092.

17. The method according to claim 12, wherein the *Lactobacillus acidophilus* is *Lactobacillus acidophilus* AM13-1 with a deposit number of GDMCC 60091.

18. The method according to claim 6, wherein the prebiotics are at least one selected from the group consisting of fructooligosaccharide, galactooligosaccharide, xylooligosaccharide, lactosucrose, soybean oligosaccharide, inulin and oligosaccharide.

19. The method according to claim 8, wherein the pharmaceutically or food acceptable carrier is at least one selected from glucose, lactose, sucrose, starch, mannitol, dextrin, glycerin fatty acid ester, polyethylene glycol, hydroxyethyl starch, ethylene glycol, polyoxyethylene sorbitol fatty acid ester, amino acid, gelatin, albumin, water and saline.

20. The method according to claim 9, wherein the food is a lactic acid drink, a soybean milk drink, a fermented food, or an animal feed.

* * * * *